United States Patent
Auld et al.

(10) Patent No.: US 8,535,268 B2
(45) Date of Patent: Sep. 17, 2013

(54) DEVICE FOR AT LEAST ONE OF INJECTION OR ASPIRATION

(75) Inventors: Jack Robert Auld, Laguna Niguel, CA (US); Brian William McDonell, Irvine, CA (US); Barry Lynn Wheatley, Oceanside, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 230 days.

(21) Appl. No.: 12/976,038

(22) Filed: Dec. 22, 2010

(65) Prior Publication Data
US 2012/0165734 A1 Jun. 28, 2012

(51) Int. Cl.
*A61M 5/28* (2006.01)
*A61M 5/315* (2006.01)

(52) U.S. Cl.
USPC ............................... 604/151; 604/224

(58) Field of Classification Search
USPC ............. 604/118, 131–155, 224, 181, 187, 604/218; 128/DIG. 1, DIG. 7, DIG. 12
See application file for complete search history.

(56) References Cited

U.S. PATENT DOCUMENTS

| | | | |
|---|---|---|---|
| 3,101,711 A | 8/1963 | Reitknecht | |
| 3,517,668 A | 6/1970 | Brickson | |
| 3,790,048 A | 2/1974 | Luciano et al. | |
| 4,022,207 A | 5/1977 | Citrin | |
| 4,230,025 A | 10/1980 | Caliri | |
| 4,270,399 A | 6/1981 | Knief | |
| 4,367,739 A | 1/1983 | LeVeen et al. | |
| 4,498,904 A | 2/1985 | Turner et al. | |
| 4,589,870 A | 5/1986 | Citrin et al. | |
| 4,659,327 A | 4/1987 | Bennett et al. | |
| 4,678,408 A | 7/1987 | Nason et al. | |
| 4,681,102 A | 7/1987 | Bartell | |
| 4,834,094 A | 5/1989 | Patton et al. | |
| 4,865,591 A | 9/1989 | Sams | |
| 4,936,833 A | 6/1990 | Sams | |
| 5,017,190 A | 5/1991 | Simon et al. | |
| 5,336,201 A | 8/1994 | von der Decken | |
| 5,354,268 A | 10/1994 | Peterson et al. | |

(Continued)

FOREIGN PATENT DOCUMENTS

| | | |
|---|---|---|
| AU | 2002242864 | 10/2002 |
| AU | 2002249383 | 10/2002 |

(Continued)

OTHER PUBLICATIONS

International Search Report for PCT/US2011/062780, dated Apr. 3, 2012, 2 pages.

(Continued)

*Primary Examiner* — Matthew F DeSanto
(74) *Attorney, Agent, or Firm* — Darien Reddick

(57) ABSTRACT

Devices, systems, and associated methods that facilitate the injection and/or aspiration of precisely controlled volumes of fluids at precisely controlled rates are provided. In some implementations, an apparatus may include a syringe and a lead screw connected to a plunger of the syringe. A ratchet gear may be connected to the lead screw. A mechanism may also be included to oscillate a frame in a direction perpendicular to a longitudinal axis of the lead screw such that one or more pawls of the frame engage the teeth of the ratchet gear in a manner that results in rotation of the ratchet gear in a single direction for controlled linear displacement of the plunger.

28 Claims, 16 Drawing Sheets

(56) References Cited

U.S. PATENT DOCUMENTS

| | | | |
|---|---|---|---|
| 5,354,333 | A | 10/1994 | Kammann et al. |
| 5,370,630 | A | 12/1994 | Smidebush et al. |
| 5,425,734 | A | 6/1995 | Blake |
| 5,468,246 | A | 11/1995 | Blake |
| 5,507,727 | A | 4/1996 | Crainich |
| 5,582,614 | A | 12/1996 | Feingold |
| 5,607,433 | A | 3/1997 | Polla et al. |
| 5,629,577 | A | 5/1997 | Polla et al. |
| 5,643,275 | A | 7/1997 | Blake |
| 5,643,276 | A | 7/1997 | Zaleski |
| 5,743,889 | A | 4/1998 | Sams |
| 5,807,346 | A | 9/1998 | Frezza |
| 5,868,728 | A * | 2/1999 | Giungo et al. .................. 606/1 |
| 5,868,751 | A | 2/1999 | Feingold |
| 5,891,153 | A | 4/1999 | Peterson |
| 5,961,496 | A | 10/1999 | Nielsen et al. |
| 6,004,297 | A | 12/1999 | Steenfeldt-Jensen et al. |
| 6,102,895 | A | 8/2000 | Cortella et al. |
| 6,162,230 | A | 12/2000 | Polla et al. |
| 6,179,843 | B1 | 1/2001 | Weiler |
| 6,235,004 | B1 | 5/2001 | Steenfeldt-Jensen et al. |
| 6,277,096 | B1 | 8/2001 | Cortella et al. |
| 6,280,449 | B1 | 8/2001 | Blake |
| 6,497,708 | B1 | 12/2002 | Cumming |
| 6,503,275 | B1 | 1/2003 | Cumming |
| 6,558,395 | B2 | 5/2003 | Hjertman et al. |
| 6,585,699 | B2 | 7/2003 | Ljunggreen et al. |
| 6,592,591 | B2 | 7/2003 | Polla et al. |
| 6,595,956 | B1 | 7/2003 | Gross et al. |
| 6,656,158 | B2 | 12/2003 | Mahoney et al. |
| 6,666,871 | B2 | 12/2003 | Kikuchi et al. |
| 6,673,049 | B2 | 1/2004 | Hommann et al. |
| 6,899,698 | B2 | 5/2005 | Sams |
| 7,066,909 | B1 | 6/2006 | Peter et al. |
| 7,195,613 | B2 | 3/2007 | Woolston |
| 7,198,615 | B2 | 4/2007 | Langley et al. |
| 7,384,413 | B2 | 6/2008 | Gross et al. |
| 7,390,314 | B2 | 6/2008 | Stutz, Jr. et al. |
| 7,513,889 | B2 | 4/2009 | Jost |
| 7,615,056 | B2 | 11/2009 | Ayton et al. |
| 7,794,430 | B2 | 9/2010 | Langley et al. |
| 7,922,695 | B2 * | 4/2011 | Wiegel et al. ................. 604/155 |
| 2001/0007075 | A1 | 7/2001 | Hjertman et al. |
| 2002/0111587 | A1 | 8/2002 | Hommann et al. |
| 2003/0040755 | A1 | 2/2003 | Meyer |
| 2003/0139749 | A1 | 7/2003 | Kikuchi et al. |
| 2003/0199824 | A1 * | 10/2003 | Mahoney et al. ............ 604/155 |
| 2003/0216745 | A1 | 11/2003 | Brady et al. |
| 2003/0236498 | A1 | 12/2003 | Gross et al. |
| 2004/0147938 | A1 | 7/2004 | Dusek et al. |
| 2004/0160575 | A1 | 8/2004 | Ayton et al. |
| 2004/0215207 | A1 | 10/2004 | Cumming |
| 2005/0055011 | A1 | 3/2005 | Enggaard |
| 2005/0085776 | A1 | 4/2005 | Hommann et al. |
| 2006/0085013 | A1 | 4/2006 | Dusek et al. |
| 2006/0229633 | A1 | 10/2006 | Shepherd |
| 2006/0229634 | A1 | 10/2006 | Shepherd |
| 2006/0247581 | A1 | 11/2006 | Pedersen et al. |
| 2006/0263511 | A1 | 11/2006 | Musch et al. |
| 2007/0043319 | A1 | 2/2007 | Kimmel et al. |
| 2008/0214996 | A1 | 9/2008 | Kimmell et al. |
| 2008/0215005 | A1 | 9/2008 | Gross et al. |
| 2008/0312605 | A1 | 12/2008 | Saiki |
| 2009/0018512 | A1 | 1/2009 | Charles |
| 2009/0105650 | A1 | 4/2009 | Wiegel et al. |
| 2009/0118738 | A1 | 5/2009 | Gerondale |
| 2009/0254045 | A1 | 10/2009 | Jost |
| 2010/0145275 | A1 | 6/2010 | Grunhut et al. |

FOREIGN PATENT DOCUMENTS

| | | |
|---|---|---|
| CA | 2439900 | 10/2002 |
| CA | 2582976 | 4/2006 |
| DE | 280192 | 11/1914 |
| DE | 836703 | 4/1952 |
| DE | 29818721 | 4/2000 |
| EP | 0270257 | 6/1988 |
| EP | 0363213 | 4/1990 |
| EP | 0295075 | 12/1991 |
| EP | 0477466 | 6/1996 |
| EP | 0673482 | 4/1998 |
| EP | 1011561 | 6/2000 |
| EP | 1003581 | 11/2000 |
| EP | 1358856 | 11/2003 |
| EP | 0925082 | 1/2005 |
| EP | 1276529 | 6/2006 |
| EP | 1698365 | 9/2006 |
| EP | 1372770 | 11/2006 |
| EP | 1372767 | 1/2007 |
| EP | 1372771 | 1/2007 |
| EP | 1799287 | 6/2007 |
| EP | 1332731 | 8/2007 |
| GB | 2224214 | 5/1990 |
| NZ | 554384 | 4/2010 |
| WO | WO 94/07562 | 4/1994 |
| WO | WO 94/15120 | 7/1994 |
| WO | WO 98/57686 | 12/1998 |
| WO | WO 01/78812 | 10/2001 |
| WO | WO 02/076536 | 10/2002 |
| WO | WO 02/076537 | 10/2002 |
| WO | WO 02/076539 | 10/2002 |
| WO | WO 02/081009 | 10/2002 |
| WO | WO 2004/035113 | 4/2004 |
| WO | WO 2004/091447 | 10/2004 |
| WO | WO 2004/112871 | 12/2004 |
| WO | WO 2005/020853 | 3/2005 |
| WO | WO 2005/070483 | 8/2005 |
| WO | WO 2006/037434 | 4/2006 |
| WO | WO 2006/113138 | 10/2006 |
| WO | WO 2006/113357 | 10/2006 |
| WO | WO 2008/020023 | 2/2008 |
| WO | WO 2008/059385 | 5/2008 |
| WO | WO 2008/155144 | 12/2008 |
| WO | WO 2010/066796 | 6/2010 |
| WO | WO 2010/066797 | 6/2010 |

OTHER PUBLICATIONS

Written Opinion of the International Searching Authority, International Application No. PCT/US2011/062780, dated Apr. 3, 2012, 6 pages.

International Search Report and Written Opinion of the International Searching Authority, International Application No. PCT/2011/062776, dated Mar. 22, 2012, 8 pages.

\* cited by examiner

DEVICE FOR AT LEAST ONE OF INJECTION OR ASPIRATION

BACKGROUND

The present disclosure relates generally to fluid delivery and, more particularly, to fluid delivery associated with ophthalmic surgery and ophthalmic drug delivery.

During ophthalmic surgery, a need exists to inject fluids into the eye at very precise volumes, at very precise flow rates, at very specific locations within the eye. Presently, ophthalmic injections are typically manually made using a conventional syringe and needle. However, such injections can lead to tissue damage, such as cause by "unsteady" injections. Additionally, the volume of material injected in this manner is difficult to control because the scale on the syringe is generally not accurate relative to the small injection volume. Accuracy of the amount of material is also reduced because of parallax error. Further, the fluid flow rates of such syringes are also difficult to control since the flow rate of material from the syringe is controlled by the force asserted by the operator. Still further, controlling an amount of material injected into the eye may be limited by the ability of the operator to accurately to stop the injection when the desired amount of material has been injected Accordingly, there exists a need for injectors, systems, and associated methods, for use in injecting materials during a medical procedure that facilitate the injection of precisely controlled volumes of fluids at precisely controlled rates.

SUMMARY

One aspect of the present disclosure encompasses a system having an elongate body defining a cavity adapted to contain a fluid. The elongate body may include a first opening in communication with the cavity. The system may also include a structure movable within the cavity. The structure may be adapted to be displaced within the cavity to expel an amount of the material from the cavity through the first opening. The system may also include a lead screw. The lead screw having a longitudinal axis may include a first portion coupled to the structure and a second portion. The system may also include a ratchet gear. The ratchet gear may include a plurality of teeth, and the ratchet gear may be coupled to the lead screw. The lead screw may be rotatable with the ratchet gear. The system may further include a frame member having a first pawl and a second pawl. The first pawl and the second pawl may be adapted to engage teeth of the ratchet gear. Additionally, the system may include an actuator operable to oscillate the frame member perpendicular to the longitudinal axis of the lead screw such that the first pawl and the second pawl engage the teeth of the ratchet gear in a manner so as to rotate the ratchet gear in a single direction.

Another aspect of the disclosure encompasses an apparatus that may include a syringe body defining a cavity. The apparatus may also include a plunger, a lead screw, a ratchet gear, a structure, and a mechanism. The plunger may be disposed within the cavity and be moveable along a length of the syringe body to dispense material from the cavity. The lead screw may be coupled to the plunger, and the ratchet gear may include a plurality of teeth. The ratchet gear may be coupled to the lead screw such that rotation of the ratchet gear causes rotation of the lead screw. The structure may include at least one pawl configured to engage the teeth of the ratchet gear. The mechanism may be operable to oscillate the structure in a direction perpendicular to a longitudinal axis of the lead screw such that oscillation of the structure perpendicular to the longitudinal axis of the lead screw causes the at least one pawl of the structure to engage the teeth of the ratchet gear in a manner that results in rotation of the ratchet gear in a single direction.

The various aspects may include one or more of the following features. The elongate body may be a syringe. The structure moveable within the cavity may be a plunger. The first opening of the elongate body may be defined by a needle. The first portion of the lead screw may be movably coupled to the structure movable within the cavity. The lead screw may be coupled to the ratchet gear such that the lead screw is slideable along the longitudinal axis relative to the lead screw. At least a portion of the lead screw may define a channel extending parallel to the longitudinal axis, and the ratchet gear may also include a protrusion. The protrusion of the ratchet gear may be received into the channel. An advancement component may also be included and be selectively engagable with the lead screw. Engagement of the advancement component with the lead screw may facilitate translation of the structure within the cavity relative to the elongate body when the lead screw is rotated.

The various aspects may also include one or more of the following features. Disengagement of the advancement component from the lead screw may allow manual translation of the lead screw relative to the elongate body without rotation of the lead screw. The lead screw may include a threaded portion. The advancement component may include a threaded portion, and the threaded portion of the lead screw and the threaded portion of the advancement component may cooperate to translate a rotation of the lead screw into a linear movement of the lead screw along the longitudinal axis. The first pawl may be positioned on a first side of the ratchet gear, and the second pawl may be positioned on a second side of the ratchet gear substantially opposite the first pawl. The actuator may be a pneumatic actuator, a hydraulic actuator, an electric actuator, or any other suitable device for generating oscillation. An example electric actuator may include a solenoid, a piezoelectric actuator, as well as other suitable electric or electromechanical devices. A control system may also be included and may be operable to control actuation of the actuator. The actuator may be in communication with the control system. The control system may include a user-actuated controller, and the controller may be operable to selectively activate the actuator. The user-actuated controller may be a foot pedal.

The various aspects may also include one or more of the following features. The control system may also include an interactive control panel. The interactive control panel may be operable to receive from a user one or more parameters associated with dispensing the material from the cavity. The one or more parameters may include at least one of a dosage volume, a maximum total dosage volume, or a flow rate. The control system may be operable to correlate the one or more parameters to at least one of a number of oscillations of the actuator or a rate of oscillation of the actuator. The frame member may include a first flexible member coupled to the first pawl and a second flexible member coupled to the second pawl. The frame member may include a first end surface and a second end surface. The first end surface and the second end surface may be formed on opposing sides of the frame member. The housing may include a bore, and the frame member may be disposed in the bore. The housing may also include a first passage adjacent to the first end surface of the frame member. The actuator may include the first end surface of the frame member and the first passage adjacent the first side of the frame member.

The various aspects may additionally include one or more of the following features. The at least one pawl may include a first pawl and a second pawl. The first pawl may be positioned on a first side of the ratchet gear, and the second pawl may be positioned on a second side of the ratchet gear substantially opposite the first pawl such that the first pawl and the second pawl alternatively engage the ratchet gear during oscillation of the structure. The mechanism may be selected from the group consisting of a pneumatic actuator, a hydraulic actuator, and an electric actuator. Example electric actuators may include, a piezoelectric actuator and a solenoid. The mechanism may be in communication with a control system that controls actuation of the mechanism. The control system may include a user-actuated controller for selectively activating the mechanism and a control panel with a user interface. The user interface may allow a user to set one or more parameters associated with dispensing the material from the cavity. The one or more parameters may include one or more of dosage volume, a maximum total dosage volume, a dispense time, and a flow rate.

The details of one or more implementations of the present disclosure are set forth in the accompanying drawings and the description below. Other features, objects, and advantages will be apparent from the description and drawings and from the claims

DETAILED DESCRIPTION

Figure 1:
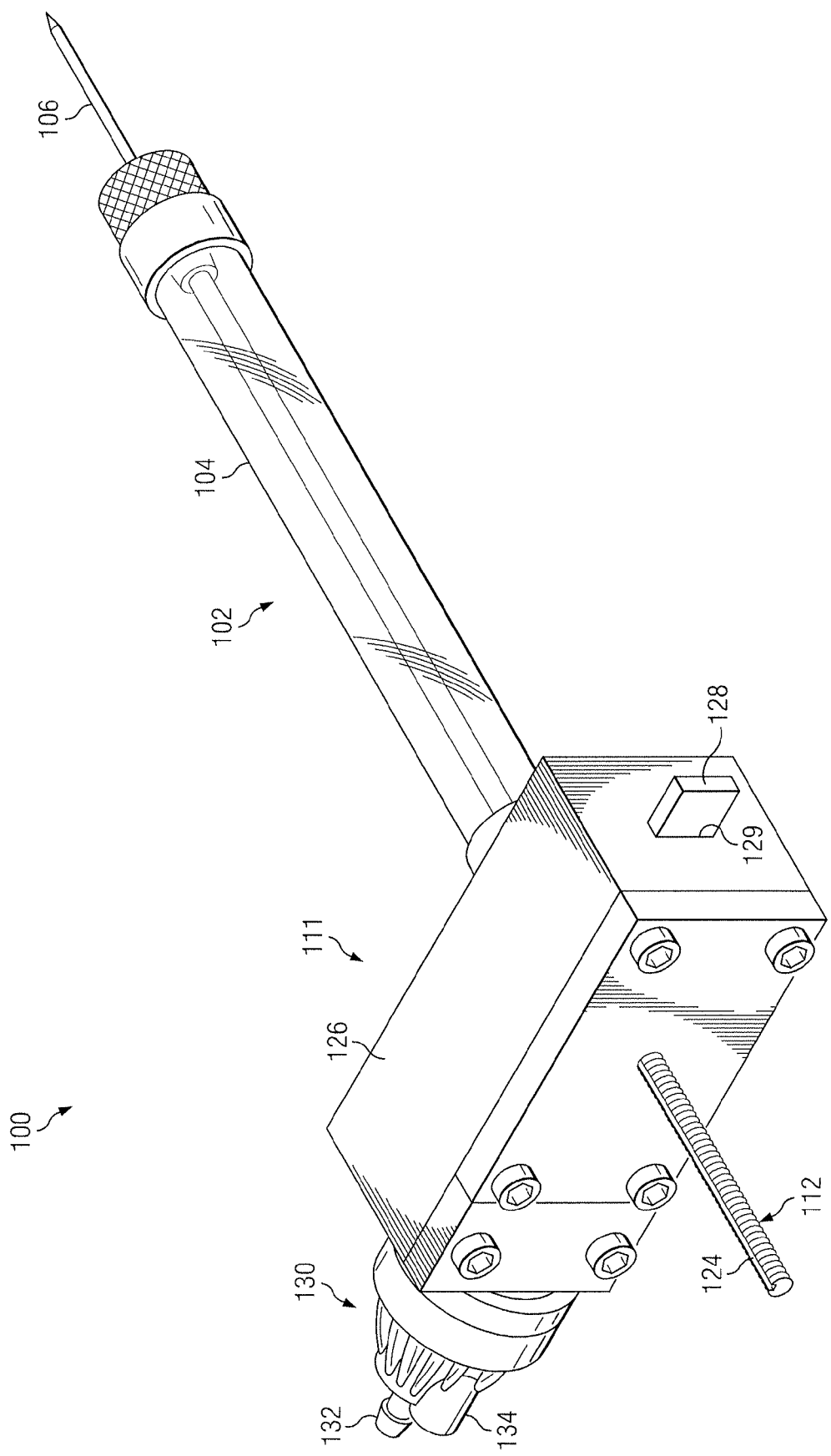
FIG. 1 is a perspective view of an example device for one of injecting or aspirating material.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation of the disclosure may be combined with the features, components, and/or steps described with respect to other implementations of the present disclosure.

The present disclosure describes devices, systems, and associated methods. The devices, systems, and methods described herein are made in the context of ophthalmic surgical procedures. However, use in ophthalmology is provided merely as an example and is not intended to be limiting. Thus, the devices, systems, and methods described herein may be applicable to numerous other fields and applications, which are intended to be encompassed by this disclosure.

In some instances, the devices and systems of the present disclosure may be utilized to deliver fluids to retinal and sub-retinal regions of a patient's eye. For example, the devices, systems, and methods described herein may be used to deliver materials such as anticoagulants, therapeutic drugs, anti-VEGF drugs, and/or any other fluids for being introduced into a patient's eye.

Figure 2:
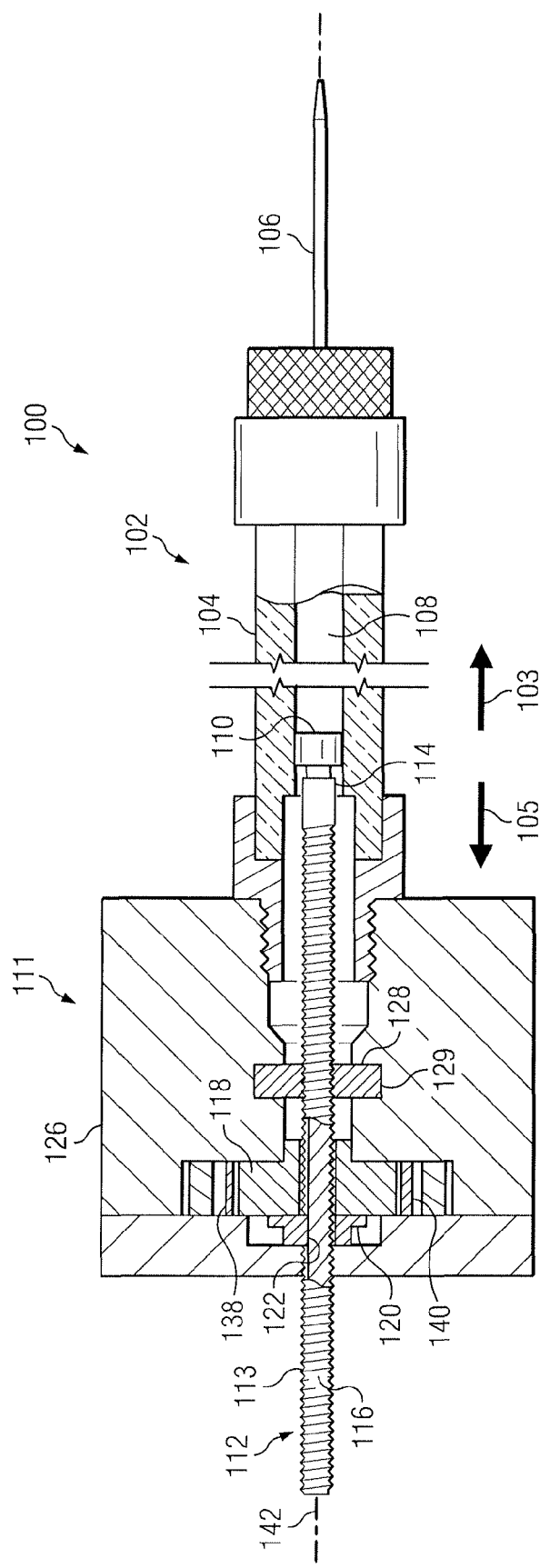
FIG. 2 is a partial cross-sectional side view of the example device of FIG. 1.

FIGS. 1-6 show an example device 100, such as for use in an ophthalmic surgical procedure. In some implementations, the device 100 may be utilized to inject material, while, in other implementations, the device 100 may be utilized to aspirate material. The device 100 may include a housing 126, a syringe 102 coupled to the housing 126, and an actuator 130 also coupled to the housing 126. The syringe 102 may include a main body portion 104 and a needle 106 extending from the main body portion. As shown in FIG. 2, the main body portion 104 may define a cavity 108 that is in communication with a lumen of the needle 106. The cavity 108 may be configured to receive a fluid that is to be dispensed from the syringe 102 through needle 106. A plunger 110 may be positioned within the cavity 108. The plunger 110 may be displaceable within the cavity 108 towards needle 106 to expel the fluid within the cavity 108 out through the needle 106. Additionally, the plunger 110 may form a seal with an inner surface of the cavity 108.

The example device 100 may also include an actuation system 111 and a ratchet mechanism 135. The ratchet mechanism 135 may include a frame 136 having pawls 138 and 140 and a ratchet gear 118. The pawls 138 and 140 of the frame 136 may cooperatively engage teeth 119 formed on the ratchet gear 118. The actuation system 111 may be coupled to the plunger 110 via the ratchet mechanism 135 to displace the plunger 110 through the cavity 108.

As shown in FIG. 2, the actuation system 111 may include a lead screw 112 having a first end 114 and a second end 116. The lead screw 112 includes a longitudinal axis 142 that extends substantially parallel and coaxial with the cavity 108 in the main body 104 of the syringe 102. The lead screw 112 includes an outer threaded surface 113. The pitch of the outer threaded surface 113 may be any desired pitch. For example, the pitch of the outer threaded surface 113 may be selected based on a desired rate of advancement of the lead screw 112 and plunger 110 through the cavity 108 for a given amount of rotation of ratchet gear 118, described in more detail below. The first end 114 of the lead screw 112 may be coupled to the plunger 110. As discussed in greater detail below, as the lead screw 112 is rotated the first end 114 of the lead screw is advanced relative to the main body 104 in the direction of arrow 103, causing the plunger 110 to move through the cavity 108 in the direction of arrow 103. In some instances, the plunger 110 may be fixedly coupled to the first end 114 of the lead screw 112 such that the plunger 110 may rotate with the lead screw 112 as the plunger 110 advances through the cavity 108. In other instances, the plunger 110 may be rotatably coupled to the first end 114 of the lead screw 112 such that the plunger 110 and the lead screw 112 are allowed to rotate relative to each other. Thus, in some implementations, the plunger 110 may not rotate with the lead screw 112, or the plunger 110 may rotate to a lesser extent than the lead screw 112 as the plunger 110 is advanced through the cavity 108.

The ratchet gear 118 may be rotatably disposed within housing 126. The second end 116 of the lead screw 112 may be coupled to the ratchet gear 118 such that rotation of the ratchet gear 118 causes rotation of the lead screw 112 while also allowing the lead screw 112 to move longitudinally relative to the ratchet gear 118. For example, in some instances, the lead screw 112 may include a channel 124, and the ratchet gear 124 may include a protrusion 122 that is retained within the slot 124. In some instances, the protrusion 122 may be formed on a ring 120 coupled to the ratchet gear 118. However, in other instances, the protrusion 122 may be integrally formed on the ratchet gear 118. In some instances, the slot 124 may extend an entire length of the lead screw 112. In other instances, the slot 124 may extend along only a portion of the entire length of the lead screw 112. Engagement between of the protrusion 122 and the slot 124 allows the lead screw 112 to be rotated with the ratchet gear 118 while, at the same time, allowing the lead screw 112 to be longitudinal slideable relative to the ratchet gear 118. As such, the lead screw 112 is able to translate relative to the ratchet gear 118 during rotation thereof.

The ratchet gear 118 may include a plurality of teeth 119. While FIGS. 3A and 6-9 show that the ratchet gear 118 includes eleven teeth 119, the ratchet gear 118 may have any number of teeth. The number of teeth 119 may be selected based on a desired fineness of controlled movement of the lead screw 112 and, thus, the plunger 110, for a given movement of the actuator 130. For example, the greater the number of teeth, the amount of movement of the lead screw 112 may be decreased for a given extension or retraction of the actuator 130. Alternately, in other implementations, the number of teeth 119 may be reduced such that an amount of movement of the lead screw 112 is increased for a given movement extension or retraction of the actuator 130. Thus, while FIGS. 4-7 illustrate the ratchet gear 118 having eleven teeth 119, it is within the scope of the disclosure that the ratchet gear 118 have more or fewer teeth 119.

Figure 4:
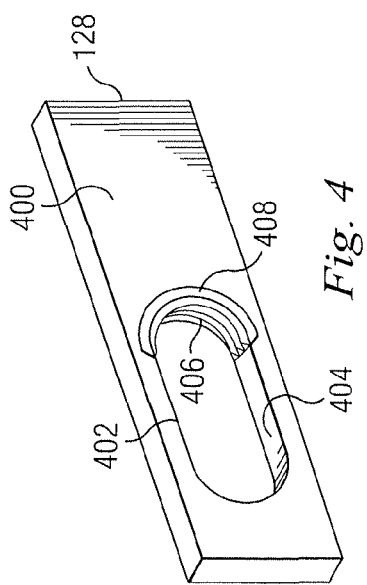
Figure 3A:
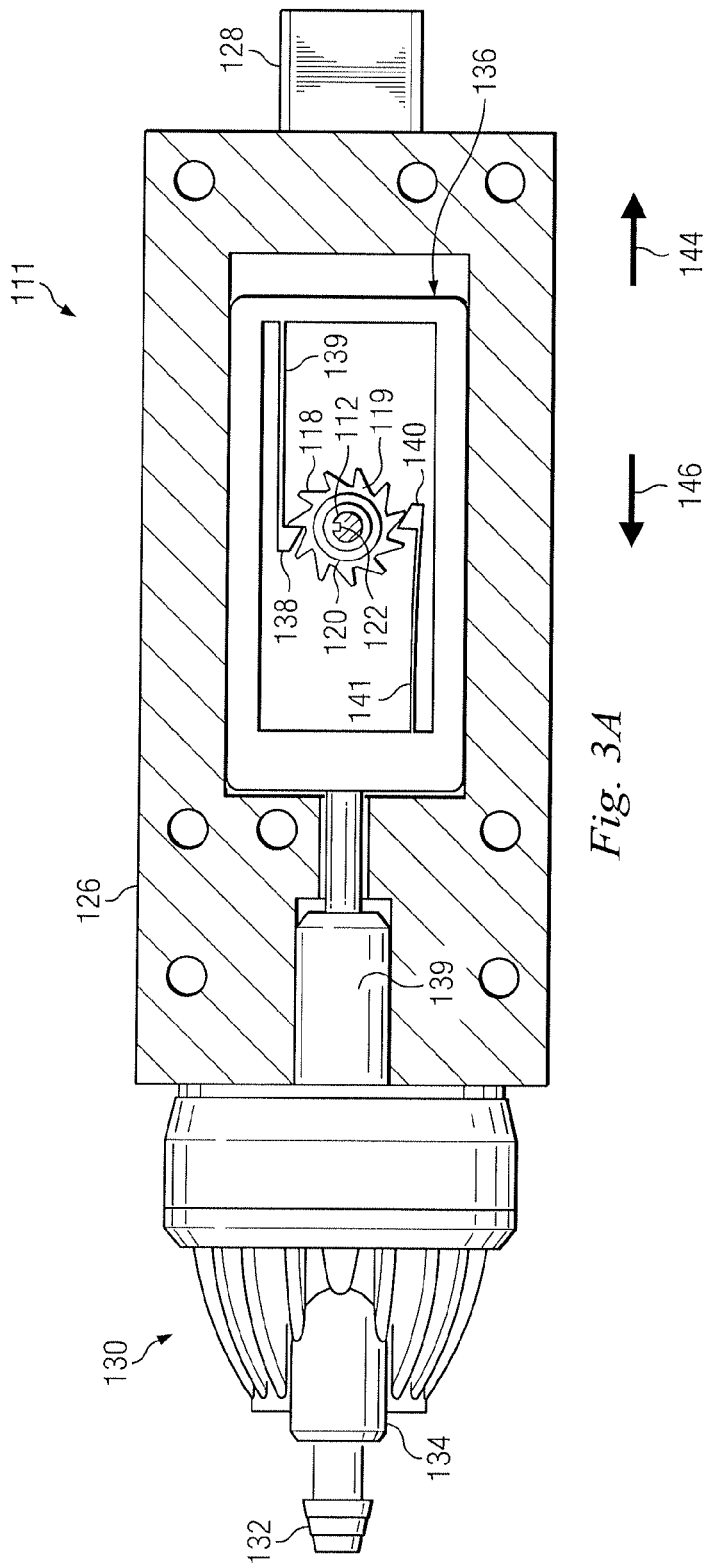
FIG. 3A is exploded partial cross-sectional view showing a ratcheting mechanism of the example device of FIG. 1.
Figure 3B:
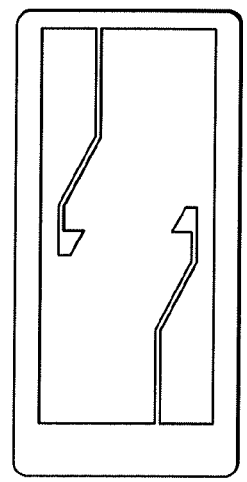
FIG. 3B shows an alternate example frame in which the flexible members are formed having a dogleg-like shape.

The device 100 may also include an advancement component half nut 128 that is slideably coupled to the housing 126. As shown in FIGS. 1-3, the advancement component 128 may be received in a slot 129. An example implementation of the advancement component 128 is shown in FIG. 4. The example advancement component 128 may include a gripping portion 400 and a slot 402. The lead screw 112 may extend through the advancement component 128 when the advancement component 128 is received in the slot 129.

An inner surface 404 of the slot 402 may include a threaded portion 406 having threads formed thereon. The threads of the threaded portion 406 may be configured to matingly engage the threads formed on the threaded surface 113 of the lead screw 112. In some implementations, the threaded portion 406 may extend along a semi-circular end of the slot 402. For example, the threaded portion 406 may extend approximately 180° along the end 408 of the slot 402. In other implementations, the threaded portion 406 may extend along more or less of the inner surface 404.

When the lead screw 112 is desired to advance through the cavity 108 of the syringe 102, a user may grip the gripping portion 400 and slide the advancement component into the slot such that the threaded portion 406 of the inner surface 404 engages the threaded surface 113 of the lead screw 112. Thus, as the lead screw 112 is rotated (such as by the ratchet mechanism, the mating threaded surfaces cause the lead screw 112 to be advanced through the cavity 108 in the direction of arrow 103 (shown in FIG. 2). When advancement of the lead screw 112 is to be prevented by actuation of the ratchet mechanism, a user may retract the advancement component 128 so that the threaded portion 406 of the inner surface 404 is disengaged from the threaded surface 113 of the lead screw 112. In such a configuration, rotation of the lead screw 112 does not cause advancement of the lead screw 112 through the cavity 108. Thus, the lead screw 112 may be freely slideable within the cavity 108 in either of directions corresponding to arrows 103, 105.

When the lead screw 112 and the advancement component 128 are not engaged, the lead screw 112 and plunger 110 may be retracted through the cavity 108 in a direction of arrow 105 (shown in FIG. 2). Sliding the lead screw 112 and plunger 110 in the direction of arrow 105 while the lead screw 112 is disengaged from the advancement component 128 may be used to load material, such as medicine or other desired materials, into the cavity 108. With the desired material is loaded into the cavity 108 the advancement member 128 may be engaged with the lead screw 112, which then allows the actuation system 111 to control the dispensing of the fluid from the syringe 102. Because of the precise control provided by the device 100 in dispensing materials therefrom, both in terms of volume and flow rate, there is less need to ensure that an exact amount of material needed for a particular procedure is loaded into the syringe 102. Rather, as long as enough material is loaded into the syringe 102, the actuation system 111 may be used to control the amount and/or rate of dispensation of the material.

Figure 5:
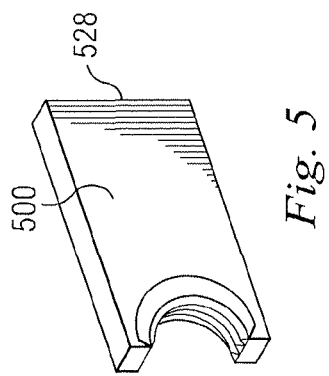
FIGS. 4 and 5 show example advancement components.

Although the advancement component 128 is shown as a member having an elongated slot, the disclosure is not so limited. Consequently, the advancement component 128 may have other forms. For example, FIG. 5 shows an alternate implementation of the advancement component 528. As shown in FIG. 5, the advancement component 128 may include a gripping portion 500 and a semi-circular recess 502. An inner surface 504 of the recess 502 may be threaded for threadably engaging the threaded surface 113 of the lead screw 112 in a manner similar to that described above. However, the advancement member 528 may be removed from the recess 129 formed in the housing 126, as the advancement member 528 does not capture the lead screw 112. Thus, in other implementations, the advancement component 128 may be a half nut.

Referring again to FIGS. 1 and 3, the actuation system 111 may also include an actuator 130. The actuator 130 may be operable to actuate the ratchet gear 118. In the example actuation system 111 illustrated in FIGS. 1 and 3, the actuator 130 is a pneumatic actuator. In other instances, the actuator 130 may be a hydraulic actuator. In still other implementations, the actuator 130 may be an electric actuator. Still further, the actuator 130 may be any suitable actuator operable to generate an oscillating action.

The actuator 130 includes ports 132 and 134 through which pneumatic pressure is alternatively cycled to actuate a member therein. For example, the actuator 130 may include a diaphragm, and the pneumatic pressure may be alternately applied to opposing sides of the diaphragm to oscillate the diaphragm. In other instances, pneumatic pressure may be applied to a single surface of the member while a bias force opposite the pneumatic pressure may be applied to the member. For example, a bias force may be applied via a spring, pressure, or in another suitable manner. Thus, pulsed pneumatic pressure applied to one side of the member within the actuator 130, in combination with the bias force, is operable to oscillate the member and, hence generate an oscillation movement of the actuator 130. While a pneumatic actuator is illustrated, it is understood that the actuator 130 may be any type of actuator capable of imparting oscillatory motion to the frame 136. For example, the actuator 130 may be a solenoid, an electro-magnetic actuator, a piezo-electric actuator, or other suitable actuator.

As shown in FIG. 3, the pneumatic actuator 130 is coupled to the frame 136 via a shaft 139. The shaft may be coupled to the actuator 130, such that the shaft 139 is made to oscillate along directions of arrows 144 and 146. As will be discussed below, the oscillating motion of the frame 136 causes rotation of the ratchet gear 118 in a single direction.

Figure 6:
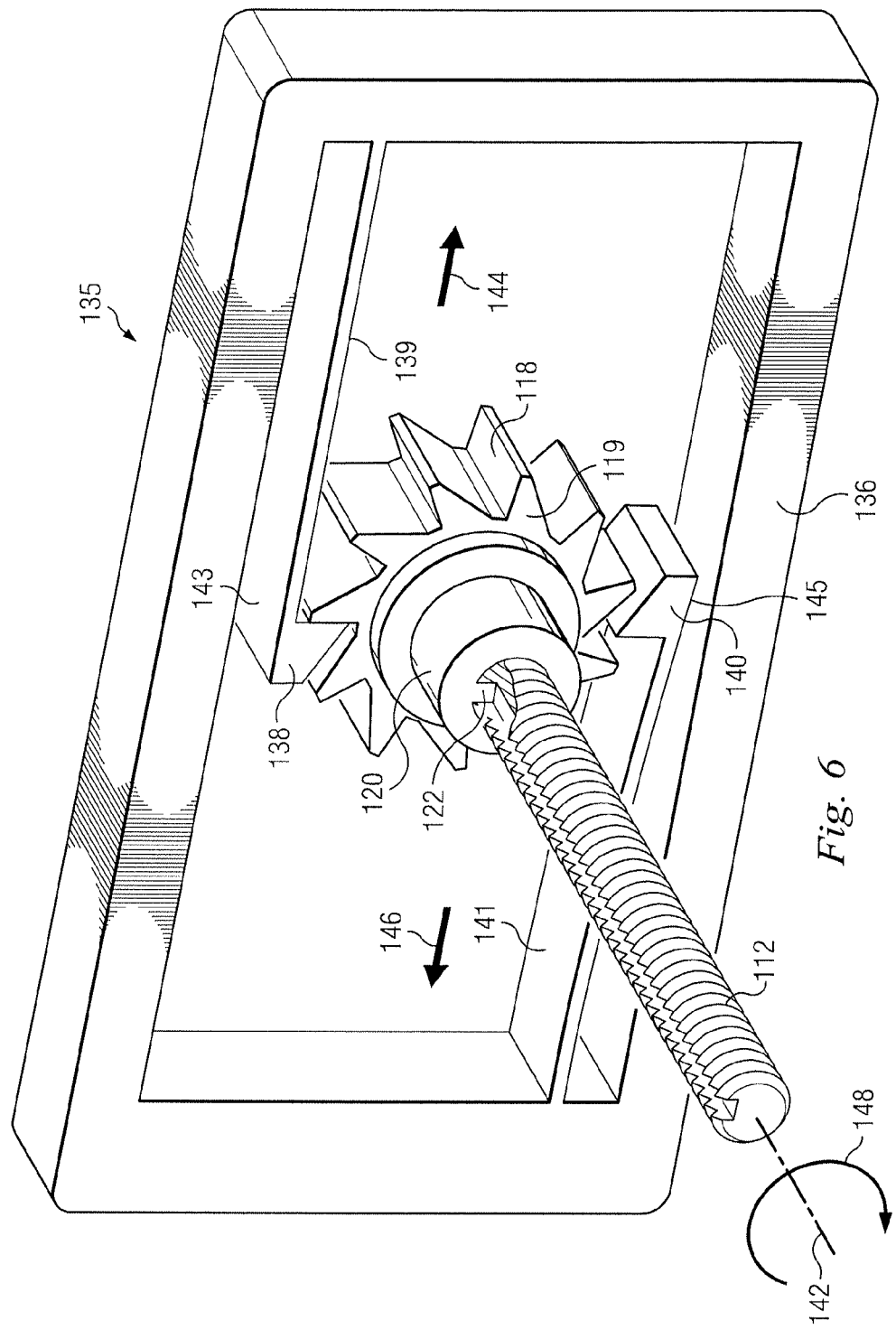
FIG. 6 is a perspective view of a portion of the ratcheting mechanism of the example ophthalmic injector system of FIG. 1.

As shown, for example, in FIG. 6, the frame 136 may include pawls 138 and 140 configured to engage the teeth 119 of the ratchet gear 118. In the example shown, the pawls 138 and 140 are formed on resilient members 139 and 141, respectively, that extend inwardly from opposing sides of the frame 136. The pawls 138 and 140 extend from ends 143 and 145, respectively, of the resilient members 139 and 141 towards the teeth 119 formed ratchet gear 118. In some implementations, the pawls 138 and 140 are disposed at approximately a 180° offset from each other. However, in other instances, the pawls 138, 140 may be angularly offset from each other by greater than or less than 180°.

Referring to FIGS. 6-9, each of the pawls 138, 140 may include a tapered leading surface 147 and a trailing surface 149, and each of the teeth 119 may include a tapered leading surface 151 and a trailing surface 153. The leading surface 147 of the pawls 138, 140 is adapted to slide along the leading surface 151 of the teeth 119, while the trailing surface 149 of the pawls 138, 140 is adapted to engage the trailing surface 153 of the teeth. As shown, the teeth 119 may also include top surface 155. However, in other implementations, the leading surface 151 and the trailing surface 153 of the teeth may intersect with each other, thereby eliminating the top surface 155. Thus, in some implementations, the top surface 155 may be included, while, in other implementations, the top surface 155 may be eliminated.

Figure 7:
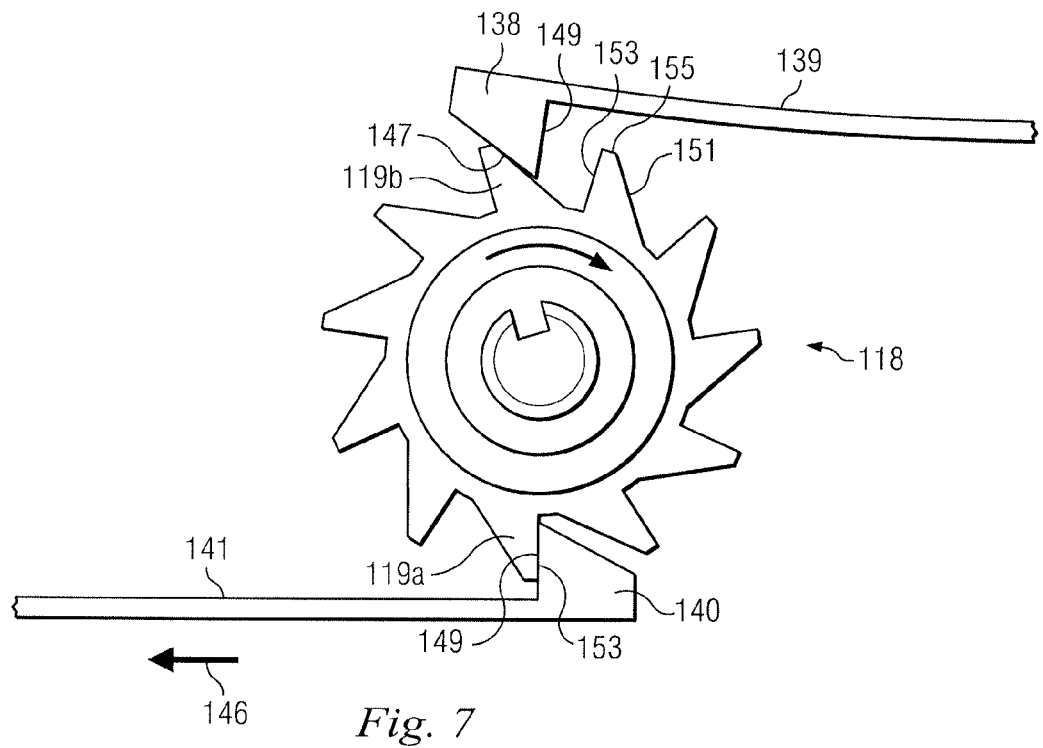
FIGS. 7 through 9 show different positions of an interface between a ratchet gear and pawls of the ratcheting mechanism.
Figure 8:
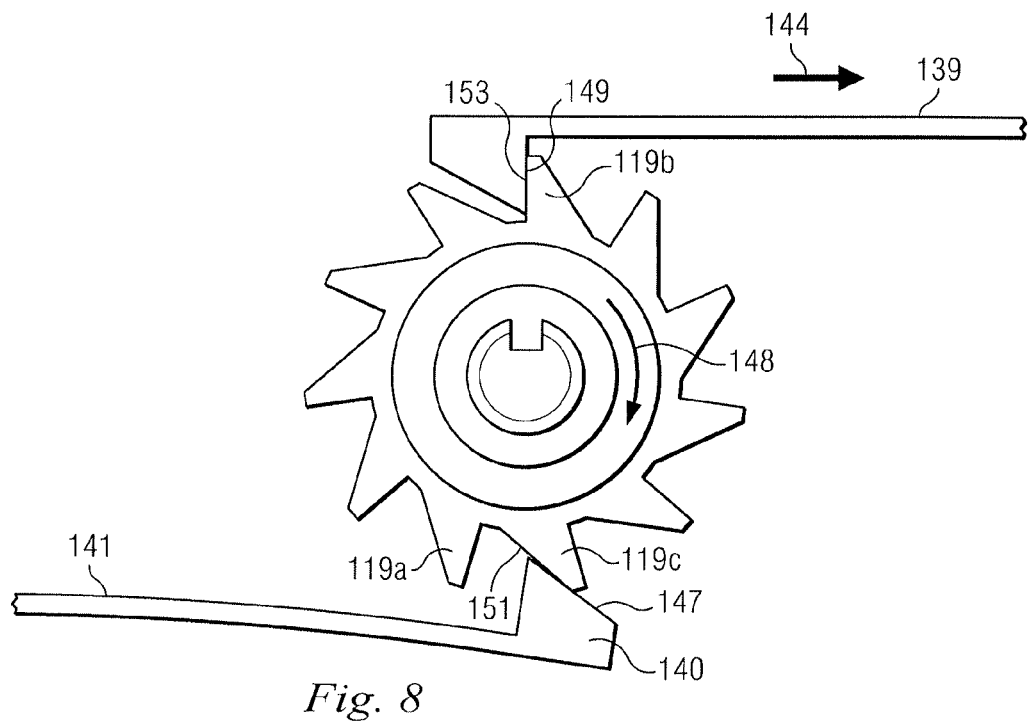
Figure 9:
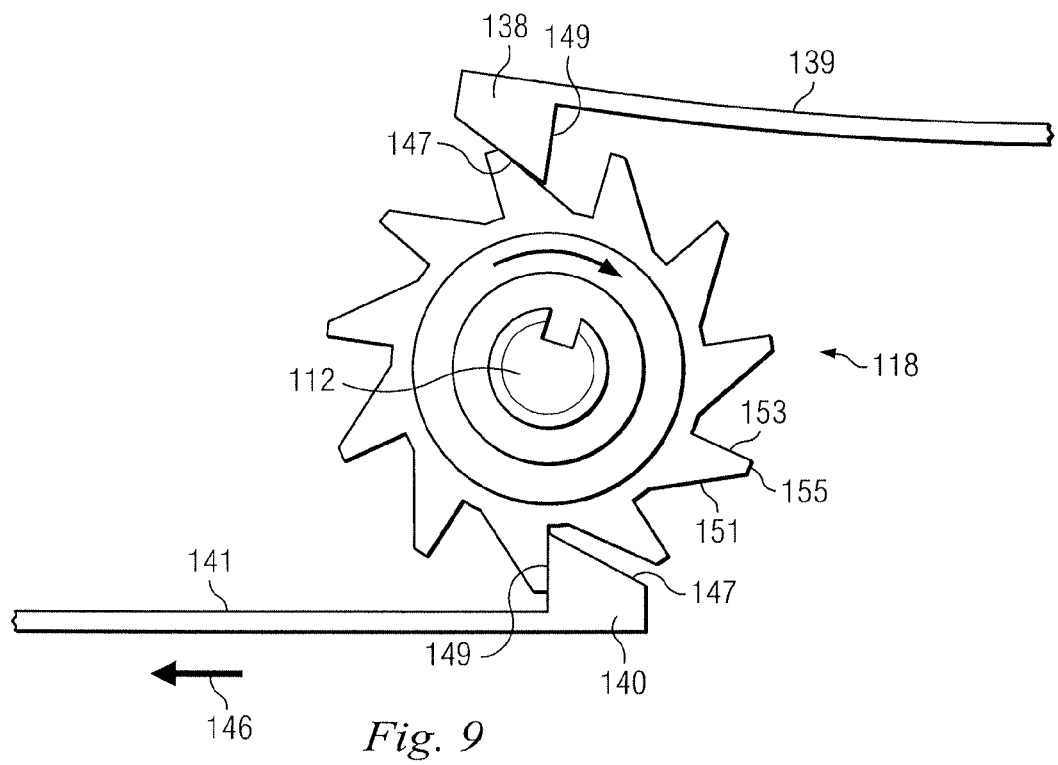

In operation, the frame 136 oscillates in opposing directions indicated by arrows 144 and 146 in response to the actuator 130, as described above. In some implementations, oscillation of the frame 136 in the directions of arrows 144 and 146 is perpendicular to the direction of the longitudinal axis 142 of the lead screw 112. As shown in FIG. 7, the trailing surface 149 of the pawl 140 is engaged with the trailing surface 153 of one tooth 119*a*, and the leading surface 147 of pawl 138 is in contact with the leading surface 151 of tooth 119*b* 155. As the frame 136 moves in the in the direction of arrow 146, the pawl 140 causes the ratchet gear 118 to rotate in a clockwise direction due to the engaging trailing surfaces 149, 153. As the ratchet gear 118 rotates, the leading surface 147 of the pawl 138 slides over the leading surface 151 and top surface 155, causing the pawl 138 to be displaced away from the ratchet gear 118 as the resilient member 139 is flexed. Once the pawl 138 extends past tooth 119*b*, the resilient member 139 biases the pawl 138 to return to an at-rest position. That is, the resilient member 139 moves the pawl 138 towards the ratchet gear 118 as flexure in the resilient member 139 is relieved. Thereafter, the trailing surface 149 of the pawl 138 faces the trailing surface 153 of tooth 119*b*, as shown in FIG. 8.

When the frame 136 reverses direction and moves in the direction of arrow 144, the trailing surface 149 of the pawl 138 engages the trailing surface 153 of tooth 119*b* so as to continue rotating the ratchet gear 118 in the clockwise direction. As the ratchet gear 118 is rotated, the resilient member 141 flexes, allowing the pawl 140 to be displaced away from the ratchet gear 118 and the leading surface 147 of the pawl 140 to slide over the leading surface 151 and top surface 155 of the tooth 119*c* until the tooth 119*c* is moved past the pawl 140. When the frame 136 reaches the end of its movement in the direction of arrow 144, the frame 136 again reverses direction and moves in the direction of arrow 146 to continue rotating the ratchet gear 118. Thus, as the frame 136 is displaced in the direction of arrow 144, pawl 138 engages a tooth of the ratchet gear 118 and causes rotation of the ratchet gear 118 in the direction of arrow 148 while pawl 140 ratchets over to the next adjacent tooth. Consequently, as the frame 136 is oscillated, the pawls 138, 140 work in cooperation to rotate the ratchet gear 118 in the same direction. Thus, oscillation of the frame 136 in the opposing directions causes the pawls 138 and 140 to engage the ratchet gear 118 in a manner that results in rotation of the ratchet gear 118 in the direction of arrow 148, clockwise as viewed in FIG. 4.

Full movement of the frame 136 in either of the directions of arrows 144 or 146 (referred to as "stroke") may be operable to cause the non-engaged pawl, i.e., the pawl whose leading surface 147 is sliding over a leading surface 151 of a tooth, to pass over a single tooth 119 of the ratchet gear 136. Further, in some implementations, such as implementations in which the ratchet gear includes eleven teeth, each movement of the frame 136 in either of the directions of arrow 144 or 146 may cause the lead screw 112 to rotate ½₂ of a revolution. In other implementations, the lead screw 112 may be rotated a greater or lesser amount. An amount of rotation of the lead screw 112 corresponding to the stroke of the frame 136 in either of the directions of arrows 144 or 146 may be defined, for example, by the size of the stroke of the frame 136 and the number of teeth 119 on the ratchet gear 118. Further, a longitudinal distance traveled by the lead screw 112 and plunger 110 along axis 142 may be defined by a pitch of the threads formed on the lead screw 112 and the advancement component 128.

As the ratchet gear 118 is rotated in response to the ratchet mechanism 135, the lead screw 112 is similarly rotated as a result the engagement of protrusion 122 and the slot 124. Accordingly, the lead screw 112 may rotate in unison with the ratchet gear 118. Further, when the advancement component 128 is engaged with the lead screw 112, the rotation of the lead screw 112 causes linear movement of the lead screw 112 (and the plunger 110) through the cavity 108 of the syringe 102 along longitudinal axis 142. Movement of the plunger 110 through the cavity 108 may be utilized to inject materials from the cavity 108, while, in other implementations, may be used to aspirate materials into the cavity 108. Further, oscillation of the frame 136 may be used to move the lead screw 112 and plunder 108 in a direction transverse to the oscillatory movement of the frame 136.

While shown as rotating the ratchet gear 118 in a clockwise direction, in other implementations, the device 100 may be operable to rotate the ratchet gear 118 in a counter-clockwise direction. Further, although the device 100 is described as being operable to inject material contained in the cavity 108 of the syringe 102, in other implementations, the device 100 may be configured so that the lead screw 112 and plunger 110 are displaceable, via operation of the ratchet mechanism 135, in the direction of arrow 105 (shown in FIG. 2) to aspirate material into the cavity 108. For example, in some instances, an example device 100 may include a lead screw 112 and an advancement component 128 with mating threads that cooperate to move the lead screw 112 in the direction of arrow 105 to aspirate materials into the cavity 108.

As explained above, the amount of advancement associated with rotation of the lead screw 112 may be dependent on the pitch of the threads formed on the threaded outer surface 113 of lead screw 112 and the corresponding threads formed on the threaded portion 406 of the advancement component 128. Thus, in some instances, the thread pitch of the threaded outer surface 113 and the threaded portion 406 may be between about 0.1 mm to 1.0 mm and, particularly, in some implementations approximately 0.2 mm to 0.6 mm. As the thread pitch is decreased, the device 100 is operable to precisely generate correspondingly smaller increments of motion because each rotation of the lead screw 112 translates into a smaller amount of linear translation of the lead screw 112 and, therefore, the plunger 110. In a similar manner, as number of teeth 119 on the ratchet gear 118 is increased, the device 100 is operable to precisely produce increasingly smaller increments of movement of the lead screw 112 and plunger 110, because each oscillation of the frame 136 causes a smaller amount of rotation of the ratchet gear 118. As a result, a smaller amount of rotation of the lead screw 112 is produced. Accordingly, the thread pitch associated with the lead screw 112 and the advancement component 128 and/or the number of teeth 119 on the ratchet gear 118 may be selected to define a desired resolution (i.e., an amount of material expelled from or aspirated into the syringe 102 per stroke of the frame 136) of the device 100.

Still further, a cross-sectional size of the cavity 108 (e.g., a diameter of the cavity 108 where the cavity 108 has a cylindrical profile) may also be selected to control an amount of material expelled from or aspirated into the syringe 102. As the size of the cavity 108 is decreased, a smaller amount of material is expelled or aspirated for a given displacement of the plunger 110. Conversely, as the cross-sectional size of the cavity 108 is increased, an increased amount of material is expelled or aspirated for a given displacement of the plunger 108.

In some implementations, the device 100 is operable to control the linear displacement of the plunger 110 in increments as small as 0.0005 inches or approximately 0.0127 mm. Also, according to some implementations, the resolution of the device 100 may be within the range of 0.02 microliters to 1.0 microliters. According to other implementations, the resolution may be less than 0.02 microliters or greater than 1.0 microliters. For example, some implementations the resolution of the device 100 may be 0.025 microliters.

In addition to precisely controlling the amount of fluid dispensed from the syringe 102, the injector device 100 may also control the flow rate at which material is dispensed from the syringe 102. For example, the flow rate may be controlled by adjusting the rate of oscillation of the frame 136. For a given device 100, the higher the rate of oscillation, the higher the rate of rotation of the ratchet gear 118, and, hence, the faster the rate of linear displacement of the plunger 110 through the cavity 108. Conversely, the lower the rate of oscillation, the lower the rate of rotation of the ratchet gear 118, and, accordingly, the lower the rate of linear displacement of the plunger 110 through the cavity 108. Accordingly, controlling the speed of oscillation of the frame 136 the device 100 may be used to control the flow rate of the material expelled from or aspirated into the syringe 102. Because actuator 130 controls the oscillation of the frame 136, the speed at which the actuator is driven actuator 130 may be used to control the rate at which material is expelled from or aspirated into the syringe 102.

In some instances, a specific flow rate may be achieved by determining the volume of fluid to be dispensed for per stroke of the frame 136 (which can be determined, for example, by the number of teeth on the ratchet gear 118, the thread pitch associated with the lead screw 112 and advancement component 128, and the profile of the cavity 108 of the syringe 102) and actuating the actuator 130 to produce a desired oscillation rate of the frame 136 (e.g., a number of oscillations per unit of time) to achieve the desired flow rate. In some instances, the device 100 may be operated to generate a flow of material by rapidly dispensing multiple discrete micro-volumes of fluid. In other implementations, the device 100 may be used to generate a flow of fluid into the syringe 102 in a similar manner. The high frequency concatenation of micro-volumes creates a relatively smooth flow of fluid with high volume accuracy and high flow rate accuracy. Accordingly, calculation of the appropriate actuation pattern for a particular flow rate can be determined based on the dispensed micro-volume of fluid for each oscillation of the frame.

For example, if the device 100 dispenses 0.0005 ml of fluid with each stroke of the frame 136, then the device 100 will dispense (or aspirate) 0.001 ml of fluid for each full oscillation of the frame (i.e., translation of the frame 136 in the direction of arrow 144 and then back in the direction of arrow 146). Accordingly, if it is desired to have 0.01 ml of fluid dispensed per second, then the actuator 130 can be adjusted to oscillate the frame at 10 full oscillations per second. Similarly, if it is desired to have 0.1 ml of fluid dispensed per second, then the actuator 130 can be adjusted to oscillate the frame at 100 oscillations per second. In some instances, the duty cycle of actuator 130 may be controlled to drive oscillation of the frame 136 at a rate corresponding to a desired flow rate of material into or out of the syringe 102. Thus, a desired flow rate for a device 100 may be determined or selected based on, for example, an oscillation rate of the actuator 130, a number of teeth 119 on the ratchet gear 118, thread pitch associated with the lead screw 112 and advancement component 128, and the profile of the cavity 108.

Figure 10:
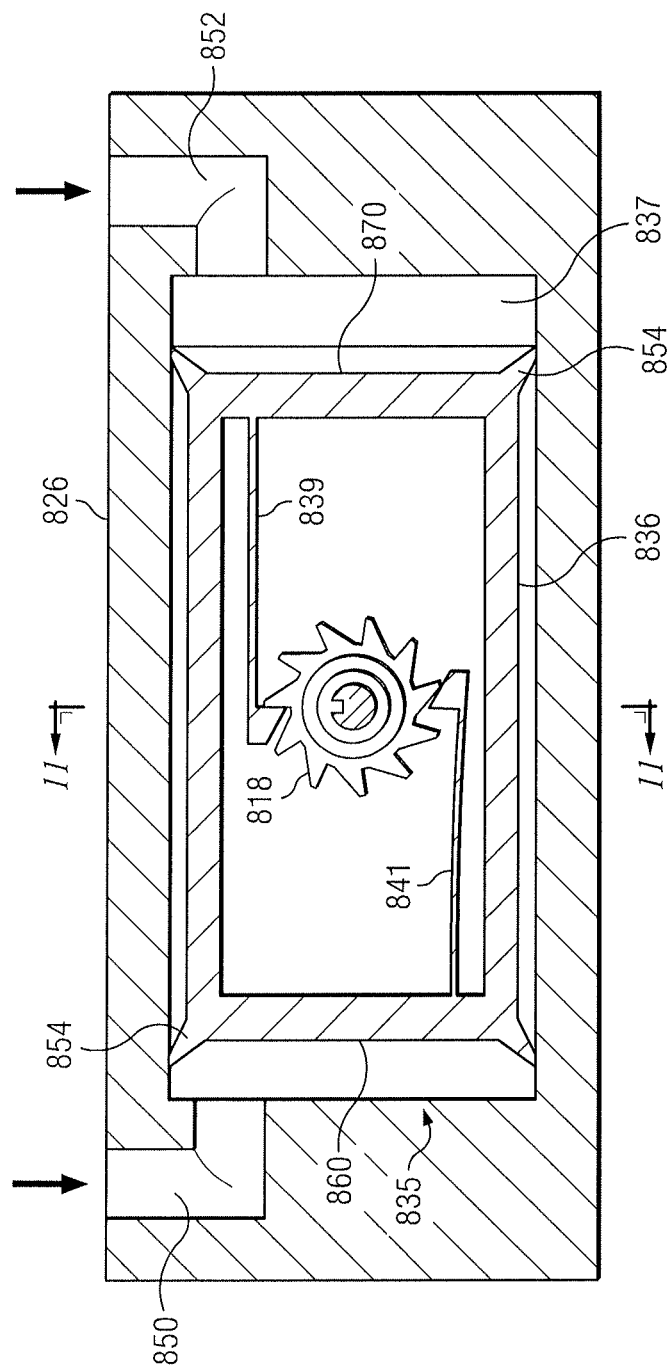
FIG. 10 shows a partial cross-sectional view of another example device according to some implementations
Figure 11:
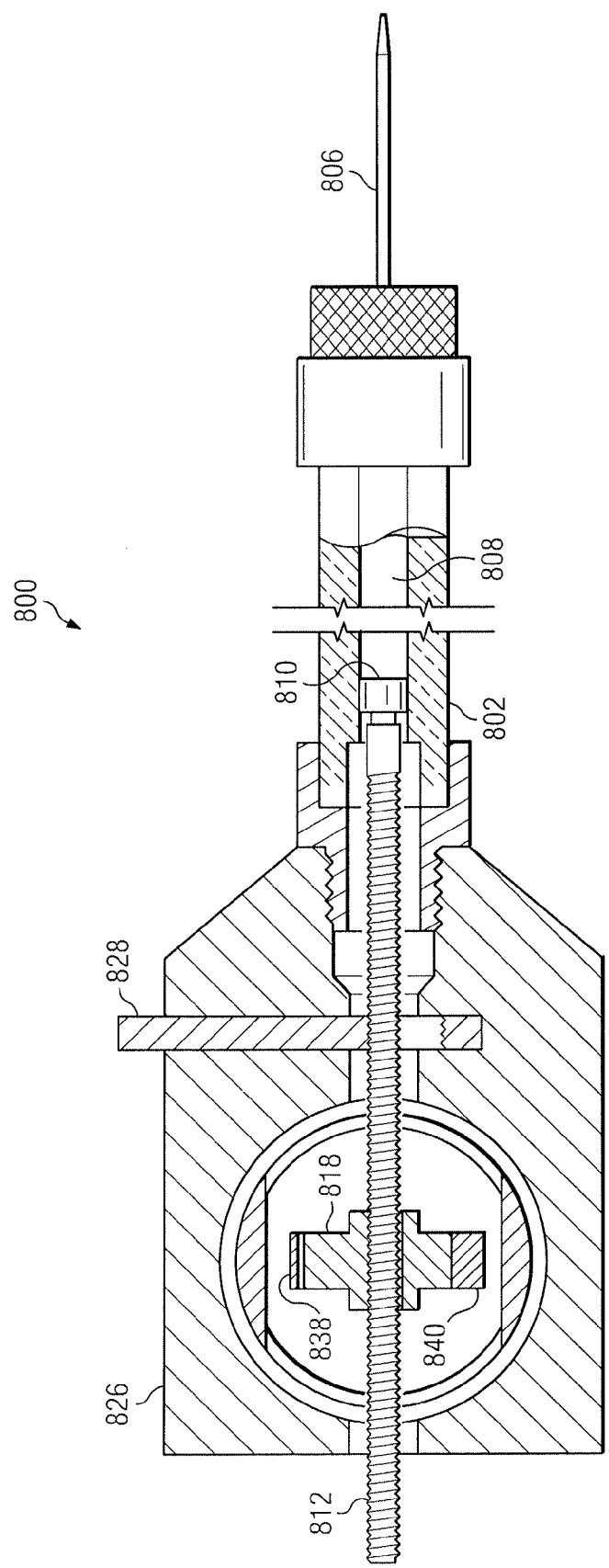
FIG. 11 shows a partial cross-sectional view of the device of FIG. 10.
Figure 12:
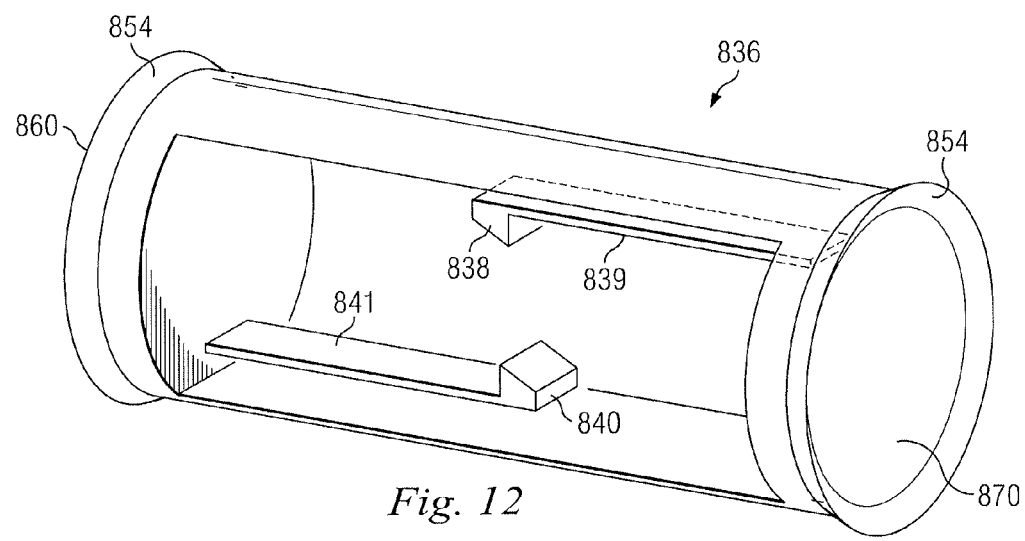
FIG. 12 shows an example frame of the device of FIG. 10.

FIG. 10 shows an example arrangement 200. In particular, the arrangement 200 may include an ophthalmic device 202 similar to device 100, discussed above. In some instances, the device 202 may be used to inject a material, such as a medicine, into a patient's eye. In other implementations, the device 202 may be used to aspirate materials from the patent's eye. The device 202 may include a dispenser 204 and a lead screw 206 coupled to the dispenser such that linear displacement of the lead screw 206 relative to the dispenser 204 may cause material to be dispensed from a cavity of the dispenser 204. Movement of the lead screw 206 may be driven by an actuator 208 that interfaces with the lead screw 206 through a coupling within housing 210 such that oscillating movement generated by the actuator 208 in a direction perpendicular to the longitudinal axis of the lead screw 206 results in rotation of the lead screw 206 in a single direction about its longitudinal axis.

As shown, the device 202 is connected to a surgical console 212. The surgical console 212 may be configured to drive the actuator 208 of the device 202 to control a volume and/or flow rate of material dispensed from the dispenser 204. In some instances, the surgical console 212 may include features, connections, and interfaces similar to those provided by the Constellation® Vision System produced by Alcon Laboratories, Inc., of 6201 South Freeway, Fort Worth, Tex. As shown, the surgical console 212 may include a cart base 214 that provides portability to the surgical console 212. The surgical console 212 may also include a connection panel 216 to provide an interface between the device 202 and the surgical console 212. A connector 218 may be used to couple the device 202 to the connection panel 216.

Connectivity provided by the connector 218 may be dependent upon the type of actuator 208 included in the device 202. For example, the connector 218 may include one or more wires, one or more cables, one or more tubes, or other connectors or the connector 218 may include of any combination of one or more wires, cables, tubes, and/or other connectors. For example, where the actuator 208 is a pneumatic actuator, the connector 218 may include one or more tubes for transmitting pneumatic to and/or from the actuator 208. In other instances, the actuator 208 may be electric. As such, the connector 218 may include one or more wires or cables, for example, to transmit electrical power and/or control signals to the actuator 208 from the surgical console 212.

As noted above, the surgical console 212 may be configured to drive the actuator 208 of the device 202 in order to control a volume and/or flow rate of material dispensed from the dispenser 204. Consequently, the surgical console 212 may include one or more processors with associated memory that may be programmed, for example, to control the actuator 208 so as to achieve the desired volume and/or flow rate. The processor(s) may take into account factors such as the desired volume, desired flow rate, number of teeth on the ratchet gear, thread pitch associated with the lead screw, and a profile of the cavity of the dispenser. The processor(s) may also utilize other information associated with one or more other factors. In some instances, a user may select a desired volume and/or desired flow. Further, in some instances, the user may select or input information regarding the parameters of the injector system 202. In other instances, information regarding the device 202 may be stored in memory carried by the device 202 that is readable by the surgical console 212 such that, when the device 202 is connected to the surgical console 212, the information can be read and utilized by the surgical console 212.

FIGS. 10-19 show other example implementations of a device that may be used to precisely control injection or aspiration of a material. Device 800 may include a housing 826 defining a bore 837, a syringe 802 coupled to the housing 826, a needle 806 coupled to the syringe 802, a lead screw 812, and an advancement component 828. The syringe 802, needle 806, lead screw 812 and advancement component 828 may be similar to and operate similarly to their counterparts described above. The housing 826 may also include a first port passage 850 and a second passage 852 that are in fluid communication with the bore 837. The syringe 802 includes a cavity 808 in fluid communication with the lumen of the needle 806. The lead screw 812 extends through the cavity 810, and a plunger 810 is coupled to the lead screw 812, such as in a manner described above with respect to the lead screw 112 and plunger 110. The device may also include a ratchet mechanism 835 including a frame 836 slideably disposed in the bore 837. The frame 836 may include a first end 860 and a second end 870. The ratchet mechanism 835 may also include a ratchet gear 818, similar to ratchet gear 118, described above.

The frame 836 may include flexible members 839, 840, similar to flexible members 139, 140. Pawls 838 and 840 are coupled to the flexible members 839, 840, respectively, and engage the ratchet gear 818 in a manner described above with respect to the pawls 138 and 140. The frame 836 may also include sealing members 854 to form a seal between an interior wall of the bore 837 and the frame 837.

In operation, a fluid, such as a pressurized gas or liquid, is alternately introduced into the passages 850, 852. The fluid pressure may act on the first end 860 and the second end 870, causing the frame 836 to oscillate within the bore 837. Oscillation of the frame 836 within the bore 837 operates the ratcheting mechanism 835 to linearly displace the lead screw 812 and plunger 810 through the cavity 808. Thus, in the illustrated implementation, the combination of passages 850, 852, the bore 837, and the frame 836 operate as an actuator to drive the lead screw 812 and plunger 810 within the device 800. Such a construction can have savings due to, for example, a simpler construction and a reduced number of parts. Further, the example device 800 may also have a reduced size, which may be desirable for procedures in a confined space. Further, a volume of the bore 837 adjacent the first end 860 and second end 870 may be minimized to reduce an amount of time needed to move the frame 836 in a particular direction. However, in other instances, the size of the volumes of the bore 837 adjacent the first end 860 and the second end 870 may be any size desired.

Figure 13:
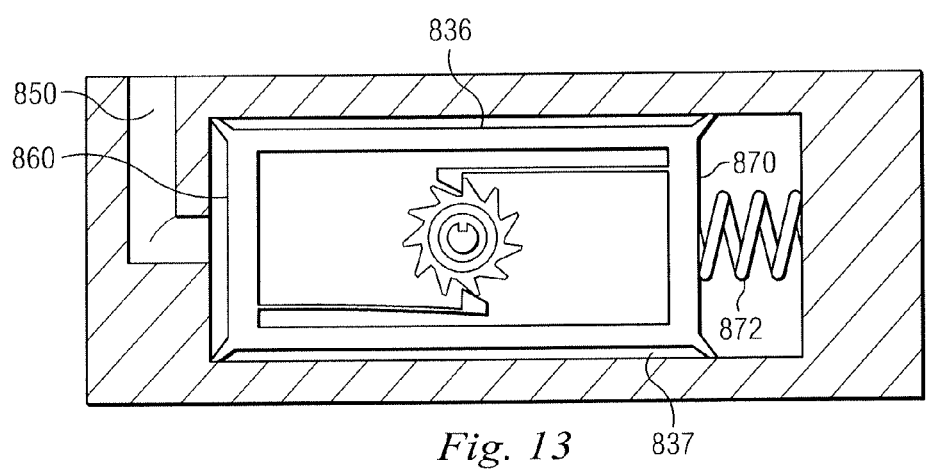
FIG. 13 show a further example implementation of a ratcheting mechanism.
Figure 14:
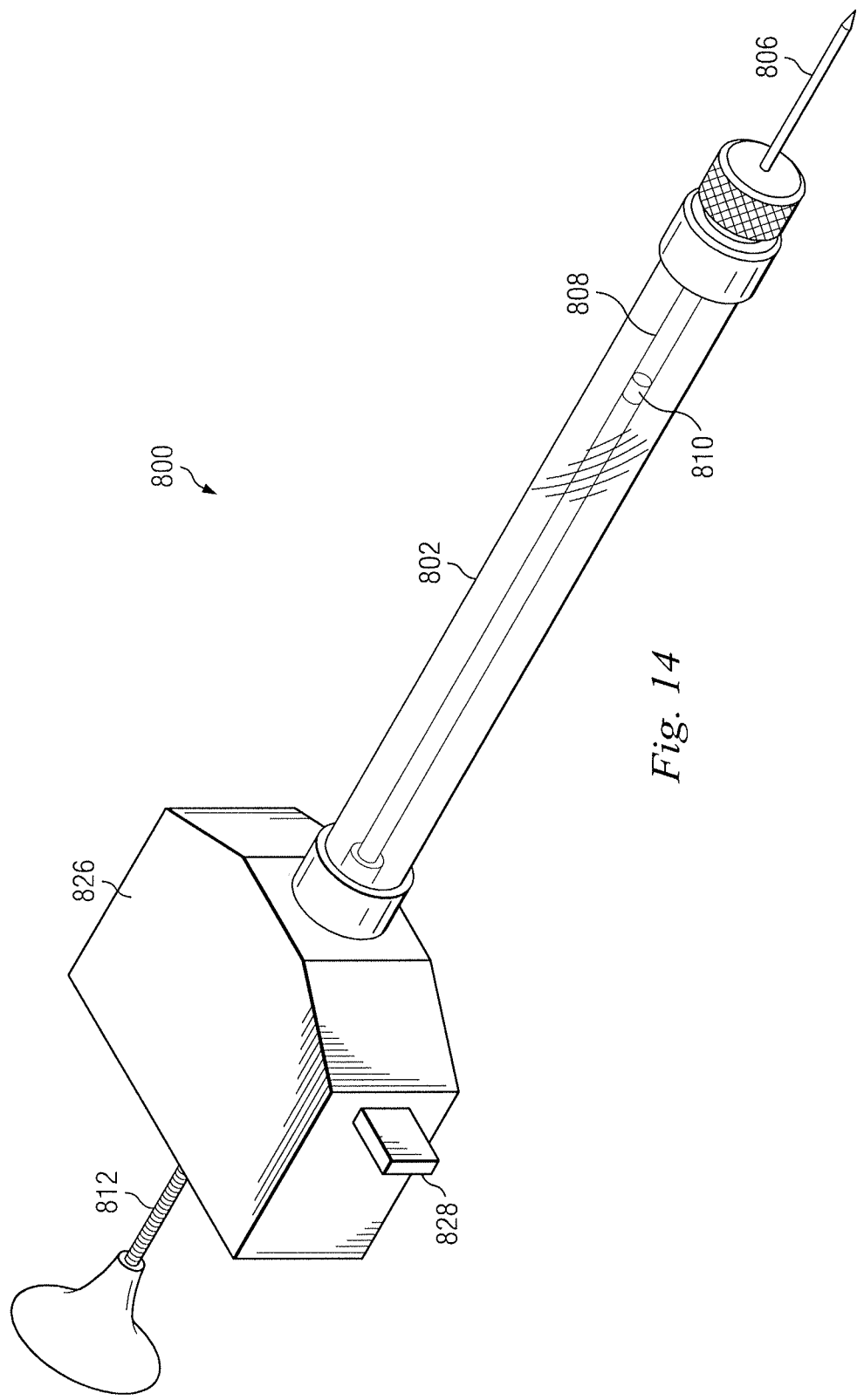
FIG. 14 is a perspective view of another example device.
Figure 15:
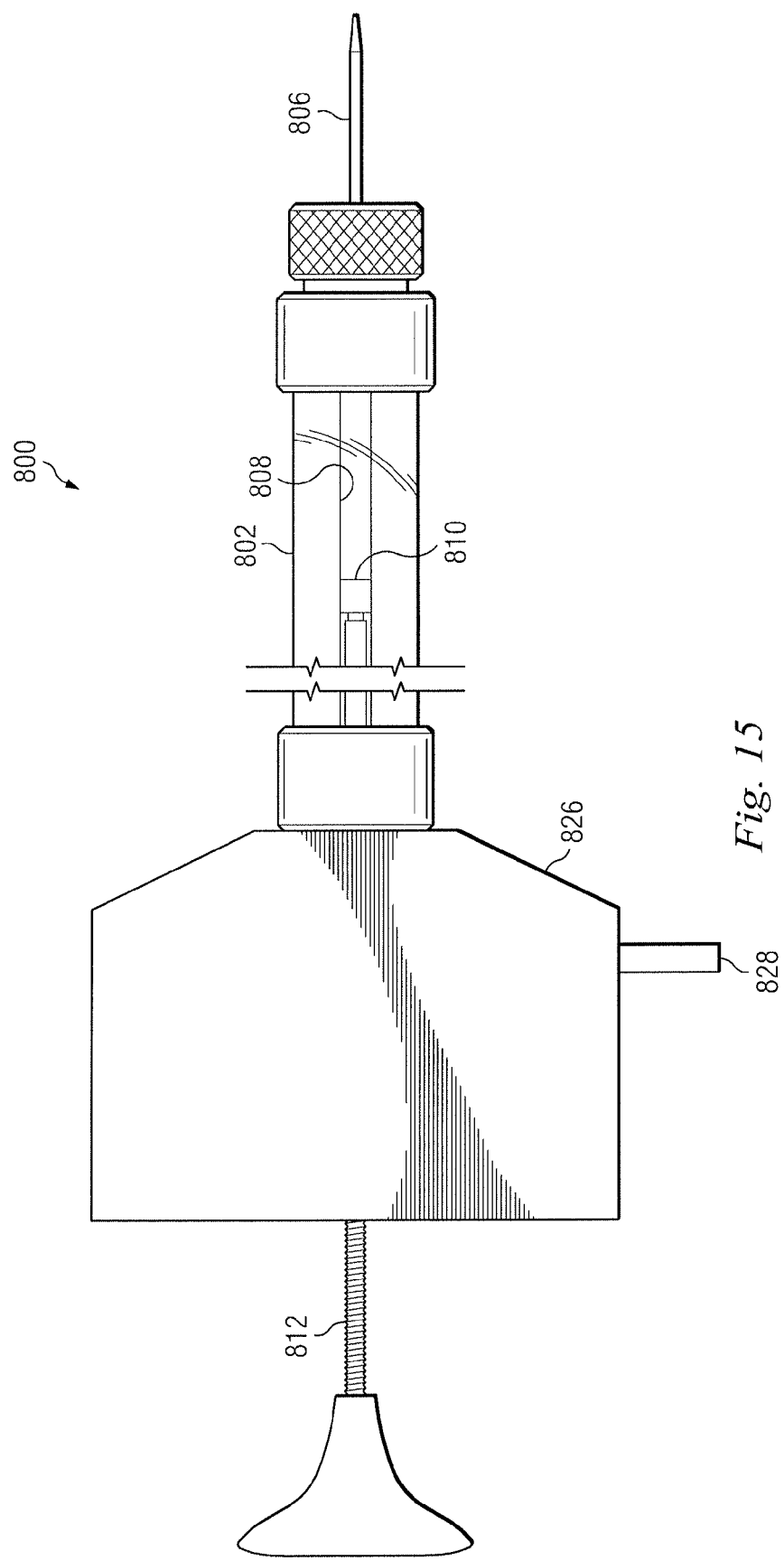
FIG. 15 is a top view of the example device of FIG. 14.
Figure 16:
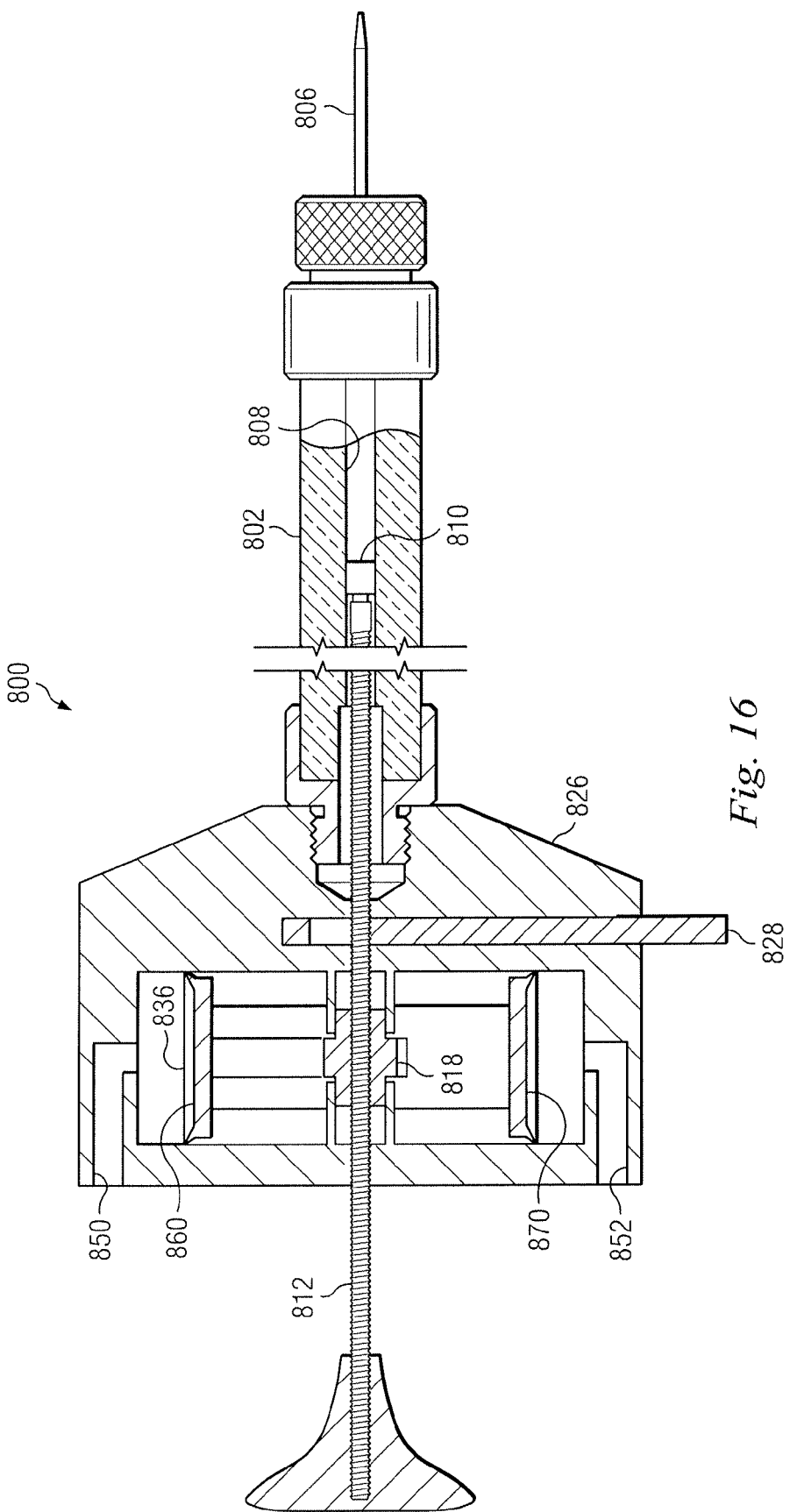
FIG. 16 is a cross-sectional view of the device of FIG. 14.
Figure 17:
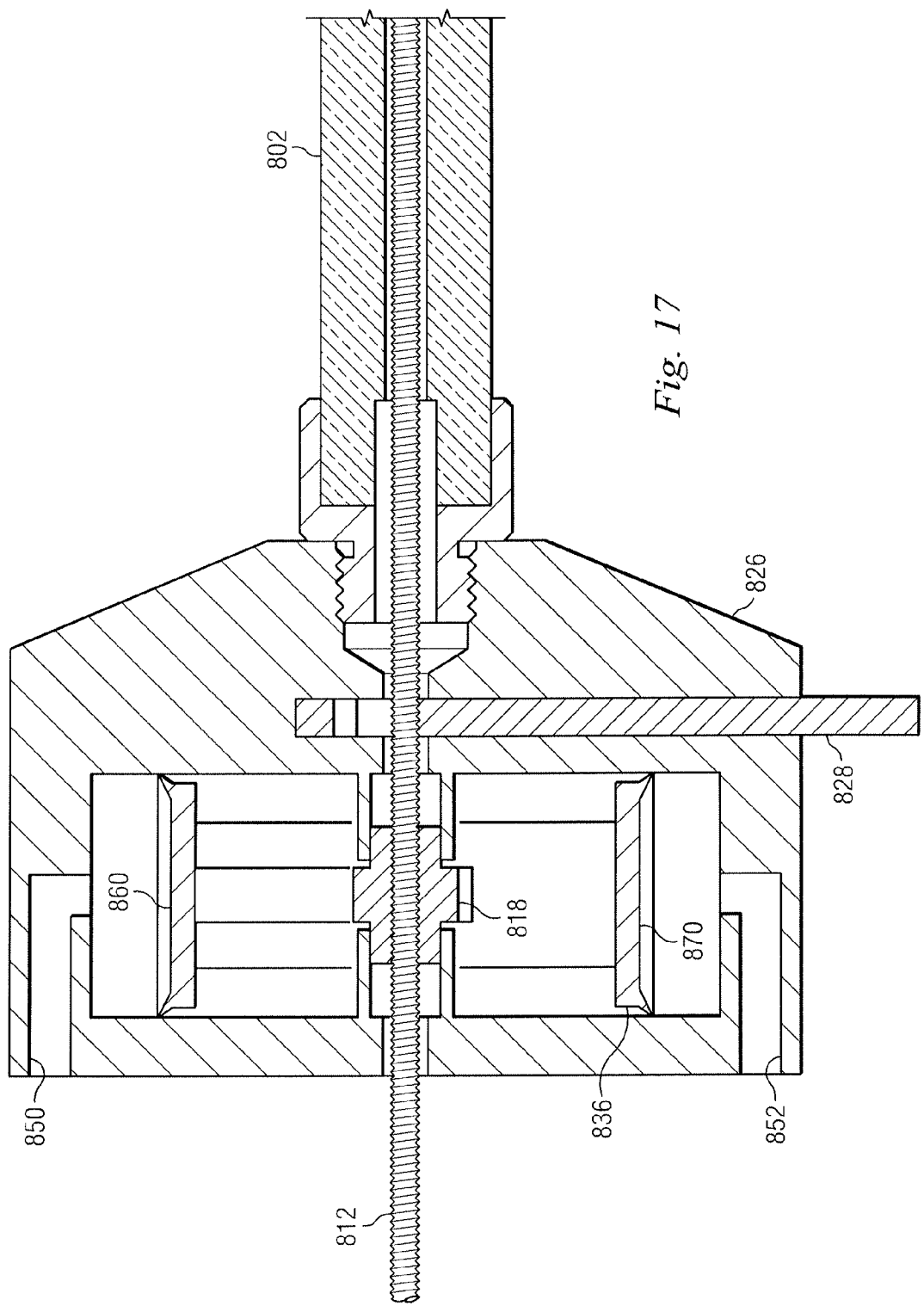
FIG. 17 is a detail view of the cross-sectional view shown in FIG. 16.
Figure 18:
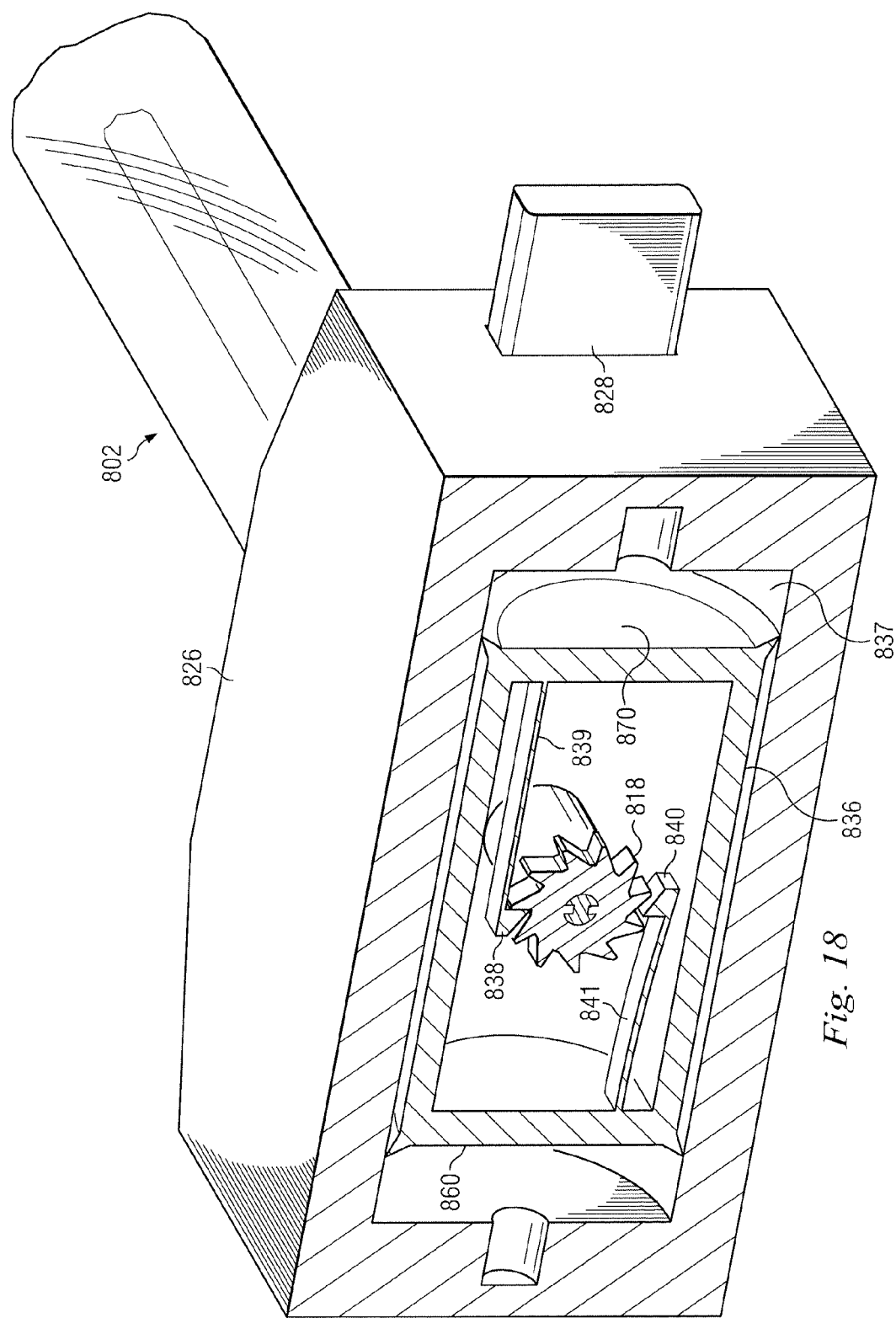
FIG. 18 is a perspective cross-sectional view of the device of FIG. 14.
Figure 19:
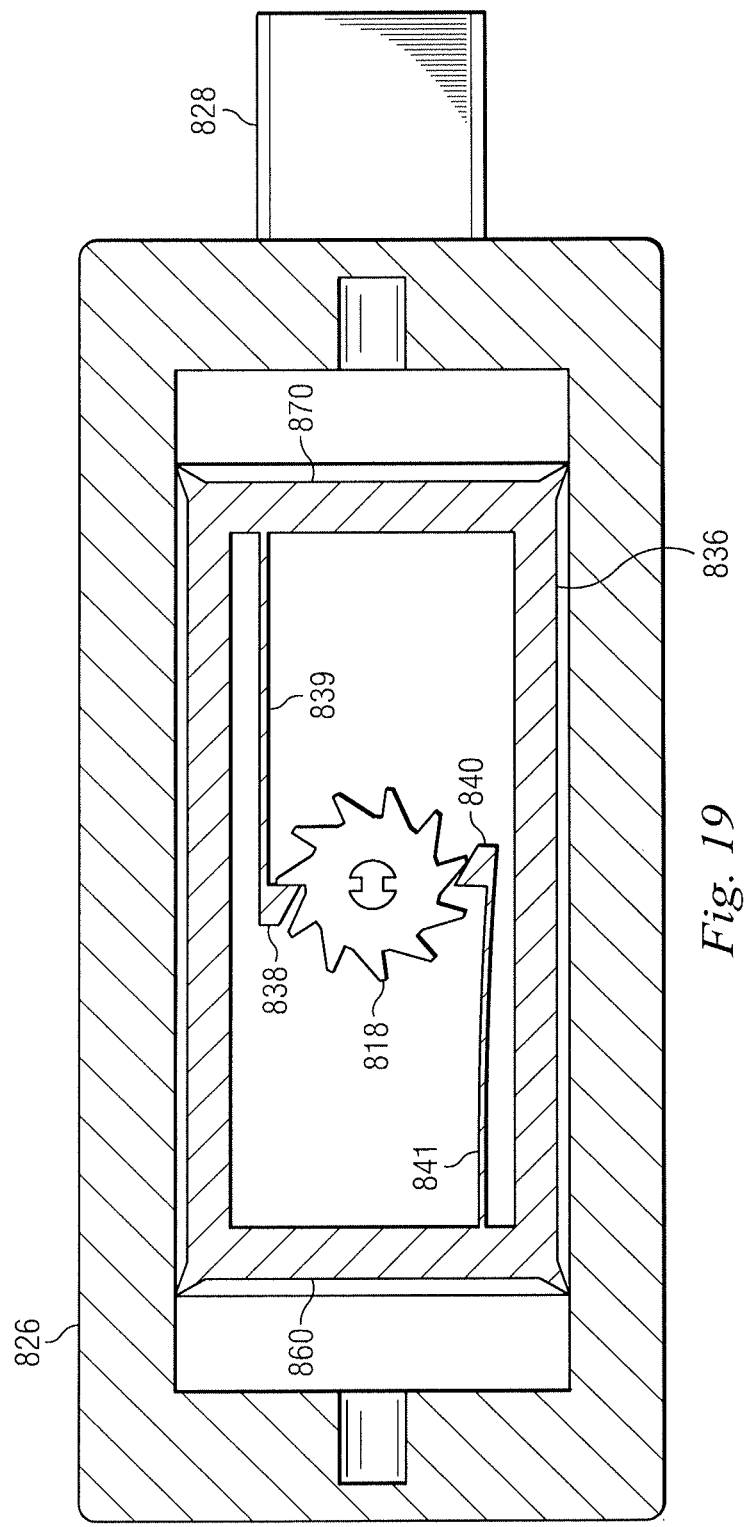
FIG. 19 is another cross-sectional view of the device of FIG. 14.

Still further, in some implementations, such as shown in FIG. 13, a single passage, such as passage 850, may be in communication with the bore 837 adjacent to the first end 860 of the frame 836. A resilient member 872 may be disposed between a second end 870 of the frame 836 and an end surface 864 of the bore 837. A vent may be in communication with the portion of the bore 837 proximate the resilient member 872 to prevent formation of a vacuum during movement of the frame 836. Thus, pulsing a fluid through the first passage 850 against the first end 860 of the frame 836 may be utilized to oscillate the frame 836, the resilient member providing a bias to act against the compressed fluid.

Although the bore 837 and frame 836 are shown as being cylindrical in shape, the disclosure is not so limited. Rather, the bore 837 and frame 836 may have any suitable shape. For example, the bore 837 and frame 836 may have any suitable cross-sectional shape.

Figure 20:
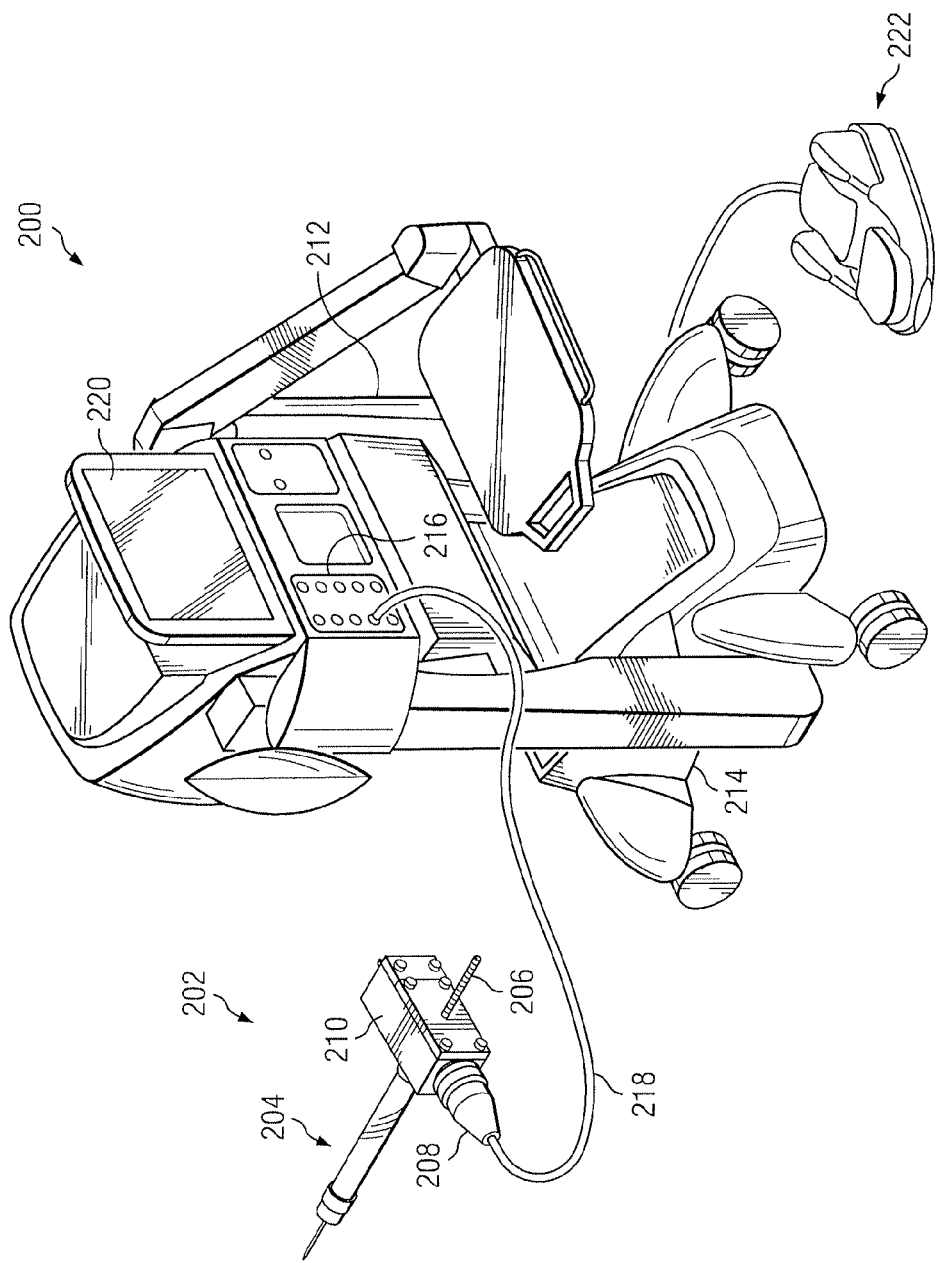
FIG. 20 shows an example ophthalmic surgical system.

As shown in FIG. 20, the surgical console 212 includes a display 220. In some instances, a user may utilize the display 220 to input or select desired information associated with the arrangement 200, such as the surgical console 212 and/or the device 202. For example, a user may interact with the display 220 or other controls of the surgical console 212 to define material volumes to be delivered by and/or aspirated into the device 202, flow rates associated with the device 202, as well as other desired parameters associated with example arrangement 200. In some instances, the surgical console 212 may include other input devices, such as a keyboard and/or mouse, to allow the user to adjust control parameters for the arrangement 200.

The surgical console 212 may be configured to provide a user with a wide range of options regarding the control of outflow or inflow of materials from or to the device 202, including, but not limit, to flow rate(s), single actuation volume, total volume, time for dispense (i.e., a preselected volume of material dispensed or aspirated in a preselected amount of time), etc. Single actuation volume, also referred to as dosage volume, is an amount of material dispensed (or aspirated) with a single actuation of a user-actuator, such as foot pedal 222. A user may control the dosage volume in order to control an amount of material dispensed (or aspirated) with each actuation of the actuator, such as foot pedal 222. This allows the user to make multiple, controlled injections or aspirations of a defined amount of material with the device 202 during a procedure. A total volume of material contained within the device 202 is understood to mean the total volume of fluid capable of being dispensed from or a total amount of material capable of being aspirated by the device 202 during a procedure, regardless of the number of times the actuator 208 has be actuated.

In some instances a user may select the desired control parameters prior to a procedure. Once the desired parameters are established, the user may control one or more aspects of the arrangement 200, such as an operation of the device 202, with the use of in input device, such as by actuating one or more mechanisms included on the foot pedal 222. For example, the foot pedal 222 may be used to cause a desired dosage and/or flow rate of material to be delivered by the system based on the selected parameters. This allows the arrangement 200 to be customized to a user's desired preferences and/or for particular types of procedures. Further, as many eye procedures are performed with the user viewing the surgical site through a microscope, the user can, in some implementations, deliver or, in other implementations, aspirate a desired amount of material and/or a desired flow rate of material while focusing on the position of the device 202 without having to look away from the microscope to adjust the device 202.

The devices, systems, and methods described herein are suitable for injection or aspiration of numerous types of materials. Examples of such materials include, without limitation, anticoagulants, therapeutic drugs, anti-VEGF drugs, short-term retinal tamponades (e.g. perfluorocarbon liquid), long-term retinal tamponades (e.g. silicone oil, air/perfluorocarbon gas mixture) used in the repair of retinal detachments or tears, anti-infectives, anti-inflammatories, anti-infective/anti-inflammatories, and/or other materials.

Although illustrative implementations have been shown and described, a wide range of modifications, changes, and substitutions are contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system, comprising:
   an elongate body defining a cavity adapted to contain a material, the elongate body comprising a first opening in communication with the cavity;
   a structure movable within the cavity, the structure adapted to be displaced within the cavity to expel an amount of the material from the cavity through the first opening;
   a lead screw comprising:
   a first portion coupled to the structure;
   a second portion; and
   a longitudinal axis;
   a ratchet gear comprising a plurality of teeth, the ratchet gear coupled to the lead screw, the lead screw being rotatable with the ratchet gear;
   a frame member comprising:
   a first pawl; and
   a second pawl, the first pawl and the second pawl adapted to engage teeth of the ratchet gear; and
   an actuator, the actuator operable to oscillate the frame member perpendicular to the longitudinal axis of the lead screw such that the first pawl and the second pawl engage the teeth of the ratchet gear in a manner so as to rotate the ratchet gear in a single direction,
   wherein at least a portion of the lead screw defines a channel extending parallel to the longitudinal axis, wherein the ratchet gear further comprises a protrusion, and wherein the protrusion of the ratchet gear is received into the channel.

2. The system of claim 1 further comprising a control system operable to control actuation of the actuator, wherein the actuator is in communication with the control system.

3. The system of claim 2, wherein the control system comprises a user-actuated controller, the controller operable to selectively activate the actuator.

4. The system of claim 3, wherein the control system further comprises an interactive control panel, the interactive control panel operable to receive from a user one or more parameters associated with dispensing the material from the cavity.

5. The system of claim 4, wherein the one or more parameters comprises at least one of a dosage volume, a maximum total dosage volume, or a flow rate.

6. The system of claim 5, wherein the control system is operable to correlate the one or more parameters to at least one of a number of oscillations of the actuator or a rate of oscillation of the actuator.

7. The system of claim 3, wherein the user-actuated controller is a foot pedal.

8. The system of claim 1 further comprising an advancement component selectively engagable with the lead screw.

9. The system of claim 8, wherein engagement of the advancement component with the lead screw facilitates translation of the structure within the cavity relative to the elongate body when the lead screw is rotated.

10. The system of claim 9, wherein disengagement of the advancement component from the lead screw allows manual translation of the lead screw relative to the elongate body without rotation of the lead screw.

11. The system of claim 8, wherein the lead screw comprises a threaded portion, wherein the advancement component comprises a threaded portion, and wherein the threaded portion of the lead screw and the threaded portion of the advancement component cooperate to translate a rotation of the lead screw into a linear movement of the lead screw along the longitudinal axis.

12. The system of claim 1, wherein the elongate body is a syringe.

13. The system of claim 12, wherein the structure movable within the cavity is a plunger.

14. The system of claim 12, wherein the first opening of the elongate body is defined by a needle.

15. The system of claim 1, wherein the actuator is a pneumatic actuator.

16. The system of claim 15, wherein the pneumatic actuator is a double acting piston.

17. The system of claim 1, wherein the first portion of the lead screw is movably coupled to the structure movable within the cavity.

18. The system of claim 1, wherein the lead screw is coupled to the ratchet gear such that the lead screw is slideable along the longitudinal axis relative to the lead screw.

19. The system of claim 1, wherein the first pawl is positioned on a first side of the ratchet gear and the second pawl is positioned on a second side of the ratchet gear substantially opposite the first pawl.

20. The system of claim 1, wherein the actuator is a hydraulic actuator.

21. The system of claim 1, wherein the actuator is an electric actuator.

22. The system of claim 1, wherein the actuator is a solenoid.

23. The system of claim 1, wherein the frame member further comprises:
   a first flexible member coupled to the first pawl; and
   a second flexible member coupled to the second pawl.

24. The system of claim 1, wherein the frame member further comprises:
a first end surface; and
a second end surface opposite the first ends surface;
wherein the housing comprises:
 a bore, the frame member disposed in the bore; and
 a first passage adjacent the first end surface of the frame member, and
wherein the actuator comprises:
 the first end surface of the frame member; and
 the first passage adjacent the first side of the frame member.

25. An apparatus comprising:
a syringe body defining a cavity;
a plunger disposed within the cavity, the plunger movable along a length of the syringe body within the cavity to dispense material from the cavity;
a lead screw coupled to the plunger;
a ratchet gear comprising a plurality of teeth, the ratchet gear coupled to the lead screw such that rotation of the ratchet gear causes rotation of the lead screw;
a structure having at least one pawl configured to engage the teeth of the ratchet gear;
a mechanism operable to oscillate the structure in a direction perpendicular to a longitudinal axis of the lead screw such that oscillation of the structure perpendicular to the longitudinal axis of the lead screw causes the at least one pawl of the structure to engage the teeth of the ratchet gear in a manner that results in rotation of the ratchet gear in a single direction; and
an advancement component selectively engagable with the lead screw, wherein the lead screw comprises a threaded portion, wherein the advancement component comprises a threaded portion, and wherein the threaded portion of the lead screw and the threaded portion of the advancement component cooperate to translate a rotation of the lead screw into a linear movement of the lead screw along the longitudinal axis.

26. The apparatus of claim 25, wherein the at least one pawl comprises:
a first pawl; and
a second pawl, the first pawl being positioned on a first side of the ratchet gear and the second pawl being positioned on a second side of the ratchet gear substantially opposite the first pawl such that the first pawl and the second pawl alternatively engage the ratchet gear during oscillation of the structure.

27. The apparatus of claim 26, wherein the mechanism is selected from the group consisting of a pneumatic actuator, a hydraulic actuator, an electric actuator, a piezoelectric actuator, and a solenoid.

28. The apparatus of claim 27, wherein the mechanism is in communication with a control system that controls actuation of the mechanism, the control system comprising:
a user-actuated controller for selectively activating the mechanism; and
a control panel with a user interface that allows a user to set one or more parameters associated with dispensing the material from the cavity, the one or more parameters including one or more of dosage volume, a maximum total dosage volume, a dispense time, and a flow rate.

* * * * *